US008882735B2

(12) United States Patent
Ong et al.

(10) Patent No.: US 8,882,735 B2
(45) Date of Patent: Nov. 11, 2014

(54) ARTICLE WITH FLUID-ACTIVATED BARRIERS

(75) Inventors: Yein Sze Ong, Singapore (SG); Meijia Ng, Singapore (SG); Priscilla Eng Choo Goh, Singapore (SG); Kwee Ling Cheng, Singapore (SG); DooHong Kim, Makati (PH); Franz Aschenbrenner, Kastl (DE)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 647 days.

(21) Appl. No.: 12/316,684

(22) Filed: Dec. 16, 2008

(65) Prior Publication Data
US 2010/0152692 A1   Jun. 17, 2010

(51) Int. Cl.
*A61F 13/475* (2006.01)
*A61F 13/472* (2006.01)

(52) U.S. Cl.
CPC ......... *A61F 13/4751* (2013.01); *A61F 13/4758* (2013.01); *A61F 13/47263* (2013.01)
USPC .............................. 604/385.28; 604/385.101

(58) Field of Classification Search
CPC ............ A61F 13/4751; A61F 13/4758; A61F 13/47263
See application file for complete search history.

(56) References Cited

U.S. PATENT DOCUMENTS

| | | |
|---|---|---|
| 2,681,032 A | 6/1954 | Shaw |
| 3,338,992 A | 8/1967 | Kinney |
| 3,341,394 A | 9/1967 | Kinney |
| 3,371,668 A | 3/1968 | Johnson |
| 3,502,538 A | 3/1970 | Petersen |
| 3,502,763 A | 3/1970 | Hartmann |
| 3,542,615 A | 11/1970 | Dobo et al. |
| 3,556,932 A | 1/1971 | Coscia et al. |
| 3,556,933 A | 1/1971 | Williams et al. |

(Continued)

FOREIGN PATENT DOCUMENTS

| | | |
|---|---|---|
| CN | D 3251084 | 8/2002 |
| EP | 0 220 741 A2 | 5/1987 |

(Continued)

OTHER PUBLICATIONS

Machine translation of Japanese Patent Publication No. 2006-334113 to Fukuhara, dated Dec. 14, 2006.*

(Continued)

*Primary Examiner* — Melanie Hand
*Assistant Examiner* — Paula L Craig
(74) *Attorney, Agent, or Firm* — Kimberly-Clark Worldwide, Inc.

(57) ABSTRACT

An absorbent article has a longitudinal direction, a transverse direction, a first major surface which forms a body-facing surface of the absorbent article, and a second major surface disposed distally from the first major surface which forms a garment-facing surface of the absorbent article. The article includes an absorbent core positioned between the first major surface and the second major surface. The article also includes at least one barrier structure having an inward-facing side and an outward-facing side, and at least one liquid shrinkable string. The at least one barrier structure is disposed on the first major surface, and the inward-facing side of the at least one barrier structure is attached to the absorbent article. In addition, a first portion of the at least one liquid shrinkable string is attached to the at least one barrier structure.

17 Claims, 8 Drawing Sheets

(56) References Cited

U.S. PATENT DOCUMENTS

| | | | |
|---|---|---|---|
| 3,692,618 A | 9/1972 | Dorschner et al. | |
| 3,802,817 A | 4/1974 | Matsuki et al. | |
| 3,849,241 A | 11/1974 | Butin et al. | |
| 4,246,900 A | 1/1981 | Schroder | |
| 4,340,563 A | 7/1982 | Appel et al. | |
| 4,357,938 A | 11/1982 | Ito et al. | |
| 4,418,524 A | 12/1983 | Ito et al. | |
| 4,447,240 A | 5/1984 | Ito et al. | |
| 4,488,928 A | 12/1984 | Ali Khan et al. | |
| 4,623,342 A | 11/1986 | Ito et al. | |
| 4,640,859 A | 2/1987 | Hansen et al. | |
| 4,675,394 A | 6/1987 | Solarek et al. | |
| 4,701,173 A * | 10/1987 | Zehner et al. | 604/385.22 |
| 4,738,677 A * | 4/1988 | Foreman | 604/385.27 |
| 4,753,646 A * | 6/1988 | Enloe | 604/385.29 |
| 4,779,456 A | 10/1988 | Cantoni | |
| 4,781,731 A | 11/1988 | Schlinger | |
| 4,787,896 A | 11/1988 | Houghton et al. | |
| 4,809,493 A | 3/1989 | Genba et al. | |
| 4,834,733 A | 5/1989 | Huntoon et al. | |
| 4,911,701 A * | 3/1990 | Mavinkurve | 604/385.25 |
| 4,942,089 A * | 7/1990 | Genba et al. | 428/364 |
| 4,981,557 A | 1/1991 | Bjorkquist | |
| 5,007,906 A | 4/1991 | Osborn, III et al. | |
| 5,008,344 A | 4/1991 | Bjorkquist | |
| 5,026,364 A * | 6/1991 | Robertson | 604/385.3 |
| 5,085,736 A | 2/1992 | Bjorkquist | |
| 5,122,407 A * | 6/1992 | Yeo et al. | 428/138 |
| 5,160,331 A * | 11/1992 | Forester et al. | 604/364 |
| 5,176,672 A | 1/1993 | Bruemmer et al. | |
| 5,181,563 A | 1/1993 | Amaral | |
| 5,260,345 A | 11/1993 | Desmarais et al. | |
| 5,330,598 A | 7/1994 | Erdman et al. | |
| 5,334,176 A | 8/1994 | Buenger et al. | |
| 5,397,316 A | 3/1995 | Lavon et al. | |
| 5,415,640 A | 5/1995 | Kirby et al. | |
| 5,447,507 A | 9/1995 | Yamamoto | |
| 5,514,121 A | 5/1996 | Roe et al. | |
| 5,520,674 A | 5/1996 | Lavon et al. | |
| 5,527,303 A | 6/1996 | Milby, Jr. et al. | |
| 5,575,785 A | 11/1996 | Gryskiewicz et al. | |
| 5,591,150 A | 1/1997 | Olsen et al. | |
| 5,593,401 A * | 1/1997 | Sosalla et al. | 604/385.28 |
| 5,779,860 A | 7/1998 | Hollenberg et al. | |
| 5,833,680 A | 11/1998 | Hartman | |
| 5,858,515 A | 1/1999 | Stokes et al. | |
| 5,885,264 A * | 3/1999 | Matsushita | 604/361 |
| 5,997,520 A | 12/1999 | Ahr et al. | |
| 6,045,900 A | 4/2000 | Haffner et al. | |
| 6,071,580 A | 6/2000 | Bland et al. | |
| 6,114,597 A | 9/2000 | Romare | |
| 6,133,501 A | 10/2000 | Hallock et al. | |
| 6,168,583 B1 | 1/2001 | Tanji et al. | |
| 6,175,056 B1 | 1/2001 | Carlucci et al. | |
| 6,217,563 B1 * | 4/2001 | Van Gompel et al. | 604/385.101 |
| D448,476 S | 9/2001 | Page et al. | |
| 6,293,935 B1 | 9/2001 | Kimura et al. | |
| D448,846 S | 10/2001 | Page et al. | |
| 6,296,628 B1 | 10/2001 | Mizutani | |
| 6,306,818 B1 | 10/2001 | Anderson et al. | |
| 6,315,765 B1 | 11/2001 | Datta et al. | |
| 6,326,525 B1 | 12/2001 | Hamajima et al. | |
| 6,346,097 B1 | 2/2002 | Blaney | |
| 6,348,047 B1 | 2/2002 | Harper | |
| 6,387,084 B1 | 5/2002 | VanGompel et al. | |
| 6,392,117 B1 | 5/2002 | Mayer et al. | |
| 6,429,261 B1 | 8/2002 | Lang et al. | |
| 6,432,097 B1 | 8/2002 | Ahr et al. | |
| 6,436,081 B1 | 8/2002 | Wada et al. | |
| 6,444,214 B1 | 9/2002 | Cole et al. | |
| 6,503,237 B1 * | 1/2003 | Lehman et al. | 604/385.28 |
| 6,521,811 B1 | 2/2003 | Lassen et al. | |
| 6,537,663 B1 | 3/2003 | Chang et al. | |
| 6,548,592 B1 | 4/2003 | Lang et al. | |
| 6,551,297 B2 | 4/2003 | Tanaka et al. | |
| 6,579,570 B1 | 6/2003 | Lang et al. | |
| 6,585,712 B2 | 7/2003 | Yoshimasa | |
| 6,599,848 B1 | 7/2003 | Chen et al. | |
| 6,620,144 B1 | 9/2003 | Glasgow et al. | |
| 6,627,670 B2 | 9/2003 | Mork et al. | |
| 6,632,205 B1 | 10/2003 | Sauer | |
| 6,653,406 B1 | 11/2003 | Soerens et al. | |
| 6,664,436 B2 | 12/2003 | Topolkaraev et al. | |
| 6,666,850 B1 | 12/2003 | Ahr et al. | |
| 6,683,143 B1 | 1/2004 | Mumick et al. | |
| 6,713,414 B1 | 3/2004 | Pomplun et al. | |
| 6,727,004 B2 | 4/2004 | Goulet et al. | |
| 6,761,709 B2 | 7/2004 | Morman et al. | |
| 6,786,893 B2 | 9/2004 | Strand | |
| 6,786,895 B1 | 9/2004 | Schmitz | |
| 6,815,502 B1 | 11/2004 | Chang et al. | |
| 6,840,925 B2 | 1/2005 | Mishima et al. | |
| 6,908,458 B1 | 6/2005 | Sauer et al. | |
| 6,955,667 B1 | 10/2005 | Tanaka et al. | |
| 6,958,430 B1 | 10/2005 | Marinelli | |
| D521,149 S | 5/2006 | Adams et al. | |
| 7,037,298 B2 | 5/2006 | Ohshima et al. | |
| 7,083,604 B2 * | 8/2006 | Sakaguchi | 604/396 |
| 7,145,054 B2 | 12/2006 | Zander et al. | |
| 7,176,344 B2 | 2/2007 | Gustafson et al. | |
| 7,179,247 B2 | 2/2007 | Mizutani et al. | |
| 7,252,870 B2 | 8/2007 | Anderson et al. | |
| 7,314,967 B2 | 1/2008 | Ashton et al. | |
| D567,369 S | 4/2008 | Gilroy | |
| 7,358,282 B2 | 4/2008 | Krueger et al. | |
| 7,491,864 B2 | 2/2009 | Nishizawa et al. | |
| D600,802 S | 9/2009 | Hood et al. | |
| D600,803 S | 9/2009 | Hood et al. | |
| D600,805 S | 9/2009 | Hood et al. | |
| 7,621,899 B2 | 11/2009 | Fujikawa et al. | |
| 7,847,145 B2 * | 12/2010 | Kurita et al. | 604/378 |
| 8,708,988 B2 * | 4/2014 | Ng | 604/385.101 |
| 2001/0029359 A1 | 10/2001 | Carlucci | |
| 2002/0128625 A1 * | 9/2002 | Tanaka et al. | 604/385.28 |
| 2002/0173768 A1 * | 11/2002 | Elsberg et al. | 604/391 |
| 2003/0050614 A1 | 3/2003 | D'Acchioli et al. | |
| 2003/0163104 A1 | 8/2003 | Tears et al. | |
| 2005/0010185 A1 | 1/2005 | Mizutani et al. | |
| 2005/0124956 A1 * | 6/2005 | Suzuki | 604/385.01 |
| 2006/0116651 A1 | 6/2006 | Kurita et al. | |
| 2006/0148917 A1 | 7/2006 | Radwanski et al. | |
| 2006/0246272 A1 | 11/2006 | Zhang et al. | |
| 2006/0282059 A1 | 12/2006 | Fujikawa et al. | |
| 2006/0287635 A1 | 12/2006 | Angel | |
| 2007/0043027 A1 | 2/2007 | Rueckle et al. | |
| 2007/0093772 A1 | 4/2007 | Koyama et al. | |
| 2007/0225671 A1 | 9/2007 | Angel | |
| 2007/0287973 A1 | 12/2007 | Cohen et al. | |
| 2008/0065035 A1 | 3/2008 | Perneborn | |
| 2008/0269703 A1 | 10/2008 | Collins et al. | |
| 2009/0036854 A1 | 2/2009 | Guidotti et al. | |
| 2009/0054760 A1 | 2/2009 | Burke | |
| 2009/0054860 A1 | 2/2009 | Young et al. | |
| 2009/0157022 A1 | 6/2009 | MacDonald et al. | |
| 2009/0157032 A1 | 6/2009 | MacDonald et al. | |
| 2009/0204095 A1 | 8/2009 | McDaniel | |
| 2009/0240220 A1 | 9/2009 | MacDonald et al. | |
| 2009/0299312 A1 | 12/2009 | MacDonald et al. | |
| 2009/0326495 A1 | 12/2009 | MacDonald et al. | |
| 2010/0147203 A1 | 6/2010 | MacDonald et al. | |
| 2010/0152642 A1 | 6/2010 | Kim et al. | |
| 2010/0152690 A1 | 6/2010 | Ong et al. | |
| 2010/0152692 A1 | 6/2010 | Ong et al. | |
| 2012/0296303 A1 * | 11/2012 | Ng et al. | 604/378 |

FOREIGN PATENT DOCUMENTS

| | | |
|---|---|---|
| EP | 0 554 565 A1 | 8/1993 |
| EP | 0 557 047 A1 | 8/1993 |
| EP | 0 815 816 A1 | 1/1998 |
| EP | 0 815 821 A2 | 1/1998 |
| EP | 0 846 454 A1 | 6/1998 |
| EP | 1 206 923 A1 | 5/2002 |
| EP | 0 869 758 B1 | 8/2002 |

(56) References Cited

FOREIGN PATENT DOCUMENTS

| | | |
|---|---|---|
| EP | EM 000772975-002 | 11/2008 |
| GB | 2 244 653 A | 12/1991 |
| GB | D 2 078 590 | 2/1999 |
| JP | 02-107249 A | 4/1990 |
| JP | 03-185197 A | 8/1991 |
| JP | 2001-017467 A | 1/2001 |
| JP | 2004-041339 A | 2/2004 |
| JP | 1233575 S | 3/2005 |
| JP | 2006-334113 A | 12/2006 |
| JP | 1318295 S | 12/2007 |
| WO | WO 94/02095 | 2/1994 |
| WO | WO 95/25493 | 9/1995 |
| WO | WO 97/14389 A1 | 4/1997 |
| WO | WO 97/40798 A1 | 11/1997 |
| WO | WO 97/40803 A1 | 11/1997 |
| WO | WO 97/46185 A1 | 12/1997 |
| WO | WO 00/00145 A2 | 1/2000 |
| WO | WO 00/53830 A1 | 9/2000 |
| WO | WO 2005/016103 A1 | 2/2005 |
| WO | WO 2006/021763 A1 | 3/2006 |
| WO | WO 2007/073254 A1 | 6/2007 |
| WO | WO 2007/125352 A1 | 11/2007 |

OTHER PUBLICATIONS

Human translation of Japanese Patent Publication No. 2006-334113 to Fukuhara, dated Dec. 14, 2006.*

* cited by examiner

ARTICLE WITH FLUID-ACTIVATED BARRIERS

BACKGROUND

Absorbent articles such as feminine care products, incontinence products, and training pants are useful to absorb and contain body wastes. These products have developed to the extent that body exudates are quickly drawn and retained away from the wearer's skin so that the wearer remains relatively dry and comfortable. Although this improved performance enhances wearer dryness and comfort, the article can still be subject to leakage, particularly during a fluid insult gush, or when the article is becoming full. In one example, adult care wearers, especially women, are very concerned about leakage in public. Some wearers may be so bothered by leakage that if it occurs in a public place, they will avoid that place and situation for the rest of their life. Leakage is therefore a very undesirable characteristic in an adult care product.

Similarly, leakage from catamenial products poses a major problem to women and can be a social embarrassment, especially if it happens in public places. Current products exist that can delay or minimize leakage through length extension, material use, etc. There exist, however, situations in which women unexpectedly experience a gush of fluid, or unknowingly wear catamenial products beyond leakage points and risk staining their clothes. A woman might also make several trips to the bathroom to check her pad for fear of leakage. Such behavior can make menstruation a more inconvenient experience than it needs to be.

In an attempt to reduce or eliminate the occurrence of leakage, it may be desirable to maintain absorbent articles in close contact with the wearer's body. Such close body fit can allow the absorbent article to absorb body exudates at their source. Achieving close body fit limits the chance for the body exudates to flow off of or out of the absorbent article. However, good body contact may not always be available, particularly along the side regions of an article, which can lead to leakage. In attempts to address this issue, leakage protection features have been included in articles. In general, such leakage protection features are typically 3-dimensional barrier structures for good body fit and to capture any excess fluid which fails to be absorbed into the pad. However, these barriers tend to add bulk to the product, while others are easily flattened during use, making the article uncomfortable, less effective, or both. Users may also be overly conscious and agitated when wearing such articles. Thus, there is a need for an absorbent article which provides close body fit and/or better leak protection, particularly after a fluid insult, without creating undesirable bulk.

SUMMARY

In response to the needs discussed above, a new absorbent article has been developed, which will allow women to maintain their active lifestyle with confidence, even on heavy-flow days. The barrier structures present in the invention have the ability to stay flat before usage, hence increasing the level of comfort to the user. Upon fluid insult, liquid shrinkable strings in the flat barrier structures shrink and pull the structures inward, causing them to lift and activate to the desired shape, forming a closer body fit, as well as a barrier to leakage. With the closer body fit, fluid has a greater tendency to be maintained within the pad, reducing the possibility of leakage.

In some aspects, the absorbent article has a longitudinal direction, a transverse direction, a longitudinally-extending centerline, a transverse-extending centerline, first and second longitudinally opposed end portions, and first and second side edges. The absorbent article comprises a first major surface which forms a body-facing surface of the absorbent article; a second major surface disposed distally from the first major surface which forms a garment-facing surface of the absorbent article; an absorbent core positioned between the first major surface and the second major surface; at least one barrier structure having an inward-facing side and an outward-facing side; and at least one liquid shrinkable string. The at least one barrier structure is disposed on the first major surface. The inward-facing side of the at least one barrier structure is attached to the absorbent article. In addition, a first portion of the at least one liquid shrinkable string is attached to the at least one barrier structure.

In some aspects, the at least one barrier structure comprises a barrier structure member selected from foam, fluff, gel, silicone, rubber, paper, nonwoven or film. In other aspects, the at least one barrier structure further comprises a wrap sheet. In yet other aspects, the barrier structure comprises a bond area. In still other aspects, the bond area is crimped.

In some aspects, the outward-facing side of the at least one barrier structure is positioned adjacent to the first side edge of the absorbent article. In other aspects, the absorbent article comprises an additional barrier structure wherein the outward-facing side of the additional barrier structure is positioned adjacent to the second side edge of the absorbent article. In yet other aspects, a second portion of the at least one liquid shrinkable string is attached to the additional barrier structure. In still other aspects, the at least one liquid shrinkable string is present as a transverse-extending stitching pattern. In yet other aspects, a spacing within the transverse-extending stitching pattern is approximately equal.

In some aspects, the at least one barrier structure is positioned on one side of the transverse-extending centerline of the absorbent article, wherein the at least one barrier structure is in a transverse orientation. In other aspects, the absorbent article further comprises an additional barrier structure positioned on another side of the transverse centerline of the absorbent article, where the additional barrier structure is in a transverse orientation. In yet other aspects, a second portion of the at least one liquid shrinkable string is attached to the additional barrier structure. In still other aspects, the at least one liquid shrinkable string is present as a longitudinally-extending stitching pattern.

In some aspects, the at least one barrier structure is positioned around a target zone of the absorbent article. In other aspects, the at least one liquid shrinkable string is present as a cross-stitching pattern. In yet other aspects, the absorbent article further comprises additional strings that are separately attached to the at least one barrier structure and to the absorbent article.

In some aspects, the absorbent article further comprises side panels for attaching the absorbent article to an undergarment. In other aspects, the absorbent article further comprises a garment fastening system for attaching the absorbent article to an undergarment.

In some aspects, the absorbent article further comprises at least one of an intake layer, a cover, a backsheet and/or a side cover. In other aspects, the absorbent article is a feminine care pad. In still other aspects, the absorbent article further comprises multiple liquid shrinkable strings.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5, as well as fractions thereof.

FIGURES

The foregoing and other features, aspects and advantages of the present invention will become better understood with regard to the following description, appended claims and accompanying drawings where:

Figure 1:
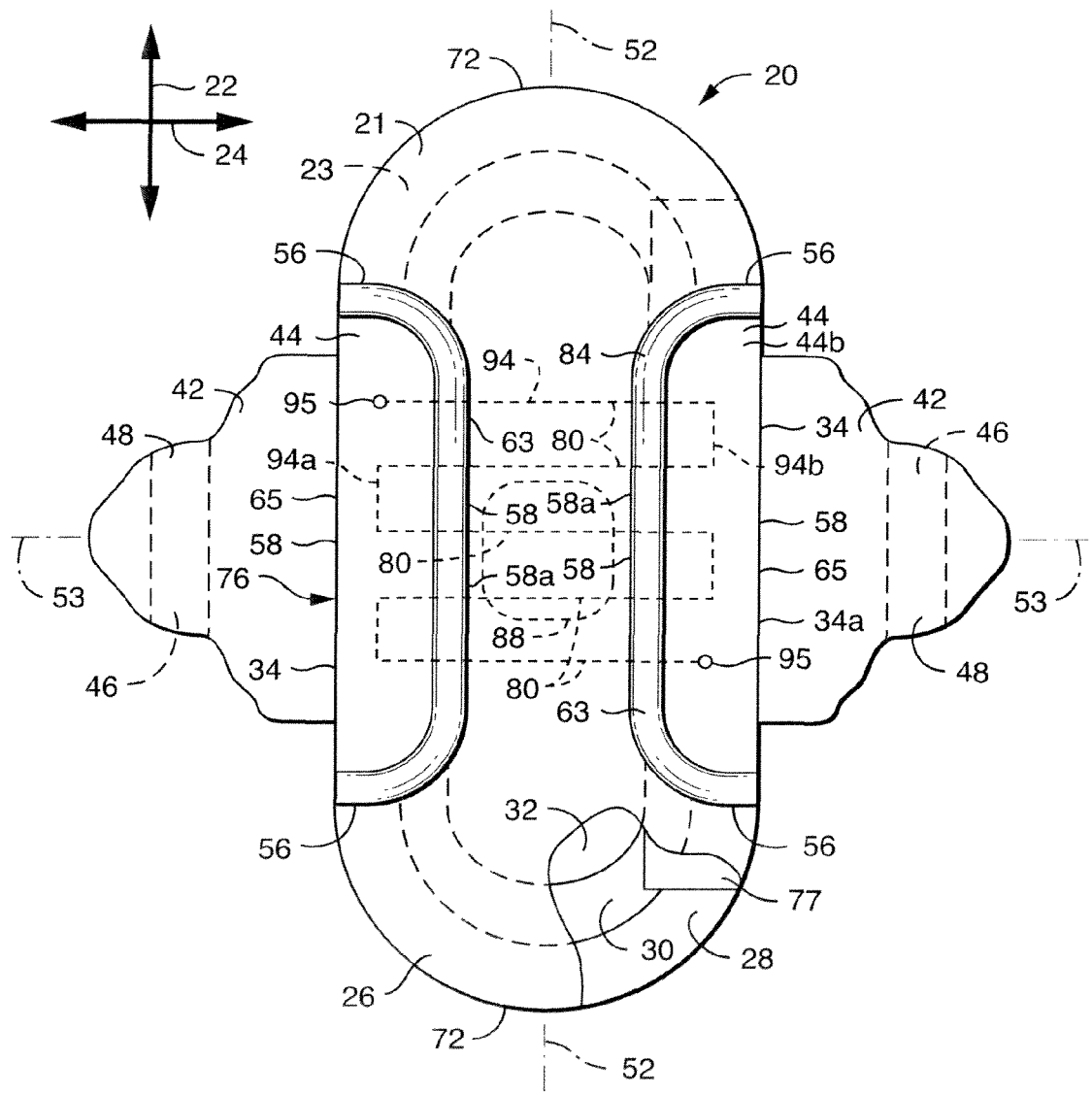
FIG. 1 is a top view of one aspect of the present invention.

Repeated use of reference characters in the present specification and drawings is intended to represent the same or analogous features or elements of the present invention.

DEFINITIONS

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain the various fluids discharged from the body.

The term "attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end wearer.

The term "bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

The term "coform" refers to a blend of meltblown fibers and absorbent fibers such as cellulosic fibers that can be formed by air forming a meltblown polymer material while simultaneously blowing air-suspended fibers into the stream of meltblown fibers. The coform material may also include other materials, such as superabsorbent materials. The meltblown fibers and absorbent fibers are collected on a forming surface, such as provided by a foraminous belt. The forming surface may include a gas-pervious material that has been placed onto the forming surface.

The term "complex liquid" describes a liquid generally characterized as being a viscoelastic liquid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption, although some components of the simple liquids may be absorbed or adsorbed more readily than others. Although a complex liquid is generally characterized herein as including specific components having inhomogeneous properties, each specific component of a complex liquid generally has homogeneous properties. Consider, for example, a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

The term "connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end wearer.

The term "disposable" is used herein to describe absorbent articles that are not intended to be laundered or otherwise restored or reused as an absorbent article after a single use.

The terms "disposed on," "disposed along," "disposed with," or "disposed toward" and variations thereof are intended to mean that one element can be integral with another element, or that one element can be a separate structure bonded to or placed with or placed near another element.

The terms "elastic," "elasticized," "elasticity," and "elastomeric" mean that property of a material or composite by virtue of which it tends to recover its original size and shape after removal of a force causing a deformation. Suitably, an elastic material or composite can be elongated by at least 50 percent (to 150 percent) of its relaxed length and will recover, upon release of the applied force, at least 40 percent of its elongation.

The term "fiber" refers to a continuous or discontinuous member having a high ratio of length to diameter or width. Thus, a fiber may be a filament, a thread, a strand, a yarn, or any other member or combination of these members.

The term "hydrophilic" describes materials which are wetted by aqueous liquids in contact with the materials. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially Equivalent system. When measured with this system, materials having contact Angles less than 90 degrees are designated "wettable" or "hydrophilic," and fibers having contact angles greater than 90 degrees are designated "nonwettable" or "hydrophobic".

The term "join" and its derivatives refer to the connecting, adhering, bonding, attaching, sewing together, or the like, of two elements. Two elements will be considered to be joined together when they are integral with one another or joined directly to one another or indirectly to one another, such as when each is directly joined to intermediate elements. "Join" and its derivatives include permanent, releasable, or refastenable joinder. In addition, the joining can be completed either during the manufacturing process or by the end wearer.

The term "layer" when used in the singular can have the dual meaning of a single element or a plurality of elements.

The term "liquid impermeable," when used in describing a layer or multi-layer laminate means that liquid, such as urine, menses or bowel movement, will not pass through the layer or laminate, under ordinary use conditions, in a direction generally perpendicular to the plane of the layer or laminate at the point of liquid contact.

The term "liquid permeable" refers to any material that is not liquid impermeable.

The term "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. In the particular case of a coform process, the meltblown fiber stream intersects with one or more material streams that are introduced from a different direction. Thereafter, the meltblown fibers and other materials are carried by the high velocity gas stream and are deposited on a collecting surface. The distribution and orientation of the meltblown fibers within the formed web is dependent on the geometry and process conditions. Under certain process and equipment conditions, the resulting fibers can be substantially "continuous," defined as having few separations, broken fibers or tapered ends when multiple fields of view are examined through a microscope at 10× or 20× magnification. When "continuous" melt blown fibers are produced, the sides of individual fibers will generally be parallel with minimal variation in fiber diameter within an individual fiber length. In contrast, under other conditions, the fibers can be overdrawn and strands can be broken and form a series of irregular, discrete fiber lengths and numerous broken ends. Retraction of the once attenuated broken fiber will often result in large clumps of polymer. Such a process is disclosed, for example, in U.S. Pat. No. 3,849,241 to Butin et al., which is hereby incorporated by reference in a manner that is consistent herewith.

The terms "nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded-carded-web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "personal care absorbent article" includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, panty liners, panty shields, interlabials, tampons, and tampon applicators; adult-care products including wipes, pads such as breast pads, containers, incontinence products, and urinary shields; clothing components; bibs; athletic and recreation products; and the like.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to, isotactic, syndiotactic, and atactic symmetries.

The terms "spunbond" and "spunbonded fiber" refer to fibers which are formed by extruding filaments of molten thermoplastic material from a plurality of fine, usually circular, capillaries of a spinneret, and then rapidly reducing the diameter of the extruded filaments.

The term "target zone" refers to an area of an absorbent article where it is particularly desirable for the majority of a fluid insult, such as urine, menses, or bowel movement, to initially contact. In particular, for an absorbent article of the present invention, the insult target zone refers to the area of the absorbent core extending a distance equal to 15% of the total length and width of the article from the insult point in all directions.

The term "thermoplastic" describes a material that softens when exposed to heat and which substantially returns to a non-softened condition when cooled to room temperature.

The term "% by weight", "weight %", "wt %" or derivative thereof, when used herein, is to be interpreted as based on the dry weight, unless otherwise specified herein.

These terms may be defined with additional language in the remaining portions of the specification.

DETAILED DESCRIPTION

Absorbent composites of this invention are useful in absorbent articles, such as disposable absorbent articles. An absorbent article of the present invention can have an absorbent core, and can additionally include a topsheet and/or a backsheet, where the absorbent core can be disposed between the topsheet and the backsheet. The articles can further include leakage barrier structures. In addition, the articles further comprise liquid shrinkable string. The barrier structures present in the article have the ability to stay flat before usage, thus increasing the level of comfort to the user. Upon fluid insult, the liquid shrinkable string, a portion of which is positioned within the barrier structure(s), shrink and pull the structures inwards (i.e., toward the longitudinal and/or transverse centerline of the article), causing it to lift and activate to a desired shape, forming a closer body fit. With the closer body fit, fluid has a greater tendency to be maintained within the pad, reducing the possibility of leakage.

To gain a better understanding of the present invention, attention is directed to the figures for exemplary purposes showing a feminine care article of the present invention. It is understood that the present invention is suitable for use with various other personal care absorbent articles without departing from the scope of the present invention.

As representatively shown in FIG. 1, by way of example, the feminine care article can be a feminine care pad or napkin. The article can have a lengthwise, longitudinal direction 22 which can extend along an appointed y-axis of the article, and a transverse, laterally extending, cross direction 24 which can extend along an appointed x-axis of the article. Additionally, the article can include first and second longitudinally opposed end portions 72, and an intermediate portion 76 located between the end portions. Generally stated, the intermediate portion 76 can be the middle 34 percent (%) of an overall, longitudinal length of the article 20. The feminine care pad 20 also has first and second side edges 34 that are the longitudinal sides of the elongated feminine care pad 20.

The side edges 34 can be contoured to match the shape of the article 20. The article 20 can have any desired shape. The feminine care article can, for example, have a dog bone shape, a race track shape, an hourglass shape, or the like. Additionally, the article can be substantially, longitudinally symmetric, or may be longitudinally asymmetric, as desired.

As representatively shown, the longitudinal dimension of the article is relatively larger than the transverse (lateral) dimension of the article. Particular configurations of the absorbent article can include an optional bodyside liner or cover 26 (also referred to as a topsheet), and/or an optional baffle or backsheet 28. The article has a first major surface 21 which forms a body-facing (bodyside) surface and a second major surface 23 disposed distally from the first major surface 21 which forms a garment-facing surface of the absorbent article. In some aspects, a cover is present which can comprise the first major surface 21 of the absorbent article. In some aspects, a backsheet is present which can comprise the second major surface 23 of the article.

Additionally, an absorbent core 30 can be present in the absorbent article. In aspects where a cover and backsheet are present, the absorbent core 30 can be positioned between the cover and backsheet. In desired arrangements, the cover can be liquid-permeable, and the backsheet can be operatively liquid-impermeable. In other arrangements, the backsheet can provide an outercover of the article. As representatively shown, for example, peripheries of the cover and backsheet may be substantially entirely coterminous. Alternatively, the peripheries of the cover 26 and the backsheet 28 may be partially or entirely non-coterminous.

The cover 26 may include a layer constructed of any operative material, and may be a composite material. For example, the cover layer can include a woven fabric, a nonwoven fabric, a polymer film, a film-fabric laminate or the like, as well as combinations thereof. Examples of a suitable nonwoven fabric include spunbond fabric, meltblown fabric, coform fabric, carded web, bonded-carded-web, bicomponent spunbond fabric, or the like, as well as combinations thereof. Other examples of suitable materials for constructing the cover layer can include rayon, bonded-carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. In desired arrangements, the cover layer can be configured to be operatively liquid-permeable.

A more particular example of a suitable cover layer material can include a bonded-carded-web composed of polypropylene and polyethylene, such as has been used as a cover stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material. In a desired arrangement, the cover 26 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, that are present or formed in the cover layer. The apertures or other openings can help increase the rate at which bodily liquids can move through the thickness of the cover layer and penetrate into the other components of the article (e.g. into the absorbent core 30).

The selected arrangement of liquid-permeability is desirably present at least on an operative portion of the cover that is appointed for placement on the body side of the article. The cover 26 can provide comfort and conformability, and can function to direct bodily exudates away from the body and toward the absorbent core 30. In a desired feature, the cover 26 can be configured to retain little or no liquid in its structure, and can be configured to provide a relatively comfortable and non-irritating surface next to the body tissues of a female wearer. The cover 26 can be constructed of any material which is also easily penetrated by bodily fluids that contact the surface of the cover layer.

The cover 26 can also have at least a portion of its bodyside surface treated with a surfactant and/or a menses modifier to increase the surface energy of the material surface or reduce the viscoelastic properties of the menses, and to render the cover more hydrophilic and more wettable to body fluids. The surfactant can permit arriving bodily liquids to more readily penetrate the cover layer. The surfactant may also diminish the likelihood that the arriving bodily fluids, such as menstrual fluid, will flow off the cover layer rather than penetrate through the cover layer into other components of the article (e.g., into the absorbent core structure). In a particular configuration, the surfactant can be substantially evenly distributed across at least a portion of the upper, bodyside surface of the cover 26 that overlays the upper, bodyside surface of the absorbent.

The cover 26, if present, may be maintained in secured relation with the absorbent core 30 by bonding all or a portion of the adjacent surfaces to one another. A variety of bonding articles known to one of skill in the art may be utilized to achieve any such secured relation. Examples of such articles include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover 26 typically extends over the upper, bodyside surface of the absorbent core, but can alternatively extend around the article to partially or entirely surround or enclose the absorbent core. Alternatively, the cover 26 and the backsheet 28 can have peripheral margins which extend outwardly beyond the terminal, peripheral edges of the absorbent core 30, and the extending margins can be joined together to partially, or entirely, surround or enclose the absorbent core.

The backsheet 28 may include a layer constructed of any operative material, and may or may not have a selected level of liquid-permeability or liquid-impermeability, as desired. In a particular configuration, the backsheet 28 may be configured to provide an operatively liquid-impermeable backsheet structure. The backsheet may, for example, include a polymeric film, a woven fabric, a nonwoven fabric, or the like, as well as combinations or composites thereof. For example, the backsheet may include a polymer film laminated to a woven or nonwoven fabric. In a particular feature, the polymer film can be composed of polyethylene, polypropylene, polyester, or the like, as well as combinations thereof. Additionally, the polymer film may be micro-embossed. Desirably, the backsheet 28 can operatively permit a sufficient passage of air and moisture vapor out of the article, particularly out of an absorbent (e.g. storage or absorbent core 30) while blocking the passage of bodily liquids. An example of a suitable backsheet material can include a breathable, microporous film, such as a HANJIN Breathable Backsheet available from Hanjin Printing, Hanjin P&C Company Limited, a business having offices located in Sahvon-li. Junganmvu.Kongiu-City, Chung cheong nam-do, Republic of South Korea. This backsheet material is a breathable film, which is dimple embossed and contains: 47.78% calcium carbonate, 2.22% TiO2, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable backsheet material can include a closed-cell polyolefin foam. For example, closed cell polyethylene foam may be employed. Still another example of a backsheet material would be a material that is similar to a polyethylene film which is used on commercially sold KOTEX brand pantiliners, and is obtainable from Pliant Corporation, a business having offices located in Schaumburg, Ill., U.S.A.

The structure of the absorbent core 30 can be operatively configured to provide desired levels of liquid retention and storage capacity, and desired levels of liquid acquisition and distribution. More particularly, the absorbent core can be configured to hold a liquid, such as urine, bowel movement, menses, other complex liquid, or the like, as well as combinations thereof. The absorbent core can include a matrix of absorbent fibers and/or absorbent particulate material to form a stabilized structure, and the absorbent fiber can include natural and/or synthetic fiber. The absorbent core may also include one or more components that can modify menses or inter-menstrual liquids.

The absorbent core 30 may also include superabsorbent material. Superabsorbent materials suitable for use in the present invention are known to those skilled in the art, and may be in any operative form, such as particulate form. Generally stated, the superabsorbent material can be a water-swellable, generally water-insoluble, hydrogel-forming polymeric absorbent material, which is capable of absorbing at least about 10, desirably about 30, and possibly about 60 times or more its weight in physiological saline (e.g., 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors, such as Evonik Stockhausen, Inc., a business having offices located in Greensboro, N.C., U.S.A. The superabsorbent material may desirably be included in an appointed storage or retention portion of the absorbent core, and may optionally be employed in other components or portions of the absorbent article.

The amount of superabsorbent material in a selected layer or other component (e.g., the absorbent core 30) can be at least a minimum of about 1 wt %. The amount of superabsorbent material can alternatively be at least about 5 wt %, and can optionally be at least about 8 wt % to provide improved performance. In other aspects, the amount of superabsorbent material can be up to a maximum of about 75 wt %, or more. The amount of superabsorbent material can alternatively be up to about 35 wt %, and can optionally be up to about 20 wt % to provide improved effectiveness.

If the amount of superabsorbent is outside the desired values, there can be excessive leakage. If the amount of superabsorbent is too high, there can be a poor containment of the superabsorbent gel and an excessive amount of gel on the wearer's skin. Additionally, the transfer of liquid to the shaping layer may be inhibited or the product may have an inadequate rate of liquid intake, causing leakage and excessive wetness against the wearer's skin. The manufacturing costs can also become excessive.

In desired configurations, the absorbent core 30 can be included in a feminine care article and can be configured to provide any operative absorbent capacity. In particular arrangements, for example, the absorbent core can provide a total, overall absorbent saturation capacity of up to about 5 grams of menses stimulant. In other arrangements, the absorbent core can provide a total, overall absorbent saturation capacity which is at least a minimum of about 5.5 grams of menses simulant (5.5 g). The overall saturation capacity can alternatively be at least about 25 grams, and can optionally be at least about 40 grams of menses simulant to provide improved performance. In a desired arrangement, the total saturation capacity of the absorbent core 30 can be up to about 107 grams of menses simulant, or more.

A suitable menses simulant is composed of swine blood diluted with swine plasma to provide a hematocrit level of 35% (by volume). A suitable device for determining the hematocrit level is a HEMATOSTAT-2 system, available from Separation Technology, Inc., a business having offices located in Altamonte Springs, Fla., U.S.A. Alternatively, a substantially equivalent device or system may be employed.

The specific saturation capacity and the specific retention capacity can be determined by soaking a 1 inch by 1 inch (2.54 cm×2.54 cm) sample of absorbent material in an amount of menses simulant that is sufficient to fully saturate the sample (e.g., 30 mL) for 30 minutes. The wet absorbent is then placed between a layer of through-air-bonded-carded web material and a layer of blotter paper, and a pressure of 0.05 psi (0.345 KPa) is applied for 1 minute to remove any pools of liquid. The saturated sample is then weighed. The weight of liquid held in the sample divided by the dry weight of the sample is the specific saturation capacity of the sample.

After the saturated sample is weighed, the absorbent sample is placed in a centrifuge and spun at 300 G for 3 minutes. The spun sample is then weighed. The weight of the liquid remaining in the spun sample divided by the dry weight of the sample is the specific retention capacity of the sample. Accordingly:

Saturation Capacity=(Wet Wt. Before Centrifuge−Dry Wt.)/(Dry Wt.)

Retention Capacity=(Wet Wt. After Centrifuge−Dry Wt.)/(Dry Wt.)

The total absorbent saturation capacity of an overall layer or other component can be determined by multiplying its specific saturation capacity times the total weight of such component. Similarly, total absorbent retention capacity of an overall layer or other component can be determined by multiplying its specific retention capacity times the total weight of such component.

A suitable through-air-bonded-carded web material has a 2.5 osy (84.8 g/m2) basis weight, a 0.024 g/cm$^3$ density, and is composed of 60 wt % of 6 denier, KoSa type 295 polyester fiber; and 40 wt % of 3 denier, Chisso ESC-HR6 bicomponent fiber. The polyester fiber is available from KoSa, a business having offices located in Charlotte, N.C., U.S.A., and the bicomponent fiber is available from Chisso Corporation, a business having offices located in Osaka, Japan. A suitable blotter paper is 100-lb white blotter paper available from Curtis Fine Papers, a business having offices located in Guardbridge, Scotland. Equivalent materials may optionally be employed.

The absorbent core 30 can be provided by a single unitary layer, or can comprise a composite structure having a selected plurality of component strata or layers. In some aspects, the absorbent core 30 is desirably a stabilized structure.

In some aspects, the feminine care pad 20 can include an optional intake layer 32, as seen in FIG. 1 for example. The intake layer 32 can help desorb liquid from the cover 26, and can help manage surges or gushes of liquid entering the article. The intake layer can also help wick or otherwise distribute liquids through the absorbent core. In desired arrangements, the intake layer can provide a temporary storage of liquid, and may provide a selected level of liquid retention. As representatively shown, the intake layer 32 can be operatively joined to the article and may be positioned between the cover 26 and the absorbent core 30.

The intake layer 32 or other supplemental layer may include natural fibers, synthetic fibers, superabsorbent materials, a woven fabric, a nonwoven fabric, a wet-laid fibrous web, a substantially unbonded airlaid fibrous web, an operatively bonded, stabilized-airlaid fibrous web, or the like, as well as combinations thereof. Additionally, the intake layer may include a selected quantity of superabsorbent materials, as desired. In a particular aspect, the fibrous material of the intake layer can be substantially free of debonding agents. The intake layer may also include one or more components that can modify menses or inter-menstrual liquid. In a particular arrangement, the intake layer 32 can be composed of a thermally-bonded, stabilized-airlaid fibrous web (e.g., Concert product code DT200.100.D0001), which is available from Concert Industries, a business having offices located in Gatineaux, Quebec, Canada.

In a desired feature, the intake layer 32 can have a desired basis weight and/or density. In particular aspects, the intake layer 32 can have a basis weight which is at least a minimum of about 30 g/m$^2$. The intake layer basis weight can alternatively be at least about 100 g/m$^2$ and can optionally be at least about 150 g/m$^2$ to provide improved performance. In other aspects, the intake layer basis weight can be up to a maximum of about 250 g/m$^2$, or more. The intake layer basis weight can alternatively be up to about 225 g/m$^2$ and can optionally be up to about 200 g/m$^2$ to provide improved performance.

If the basis weight of the intake layer 32 is outside the desired values, the article can be too thick and bulky, and can provide poor comfort and excessive awareness of the article during use. An overly high basis weight can excessively decrease the amount of liquid transferred to the absorbent core 30, can undesirably increase the amount of liquid held in the intake layer and/or can be excessively expensive. An overly low basis weight can excessively limit the ability to acquire, temporarily store and transfer liquid, and can permit premature leakage. If the basis weight of the intake layer is outside the desired values, the article can also exhibit an excessively high rewet or flowback to the wearer's skin and provide an undesired wet, moist feel to the wearer. Additionally, the intake layer can present an excessively low void volume to subsequent inputs of liquid, and the low void volume can contribute to premature leakage and excessive rewet or flowback to the wearer's skin.

In other aspects, the intake layer 32 can have a density which is at least a minimum of about 0.01 g/cm$^3$. The intake layer density can alternatively be at least about 0.02 g/cm$^3$ and can optionally be at least about 0.04 g/cm$^3$ to provide improved performance. In other aspects, the intake layer density can be up to a maximum of about 0.14 g/cm$^3$, or more. The intake layer density can alternatively be up to about 0.10 g/cm$^3$ and can optionally be up to about 0.08 g/cm$^3$ to provide improved performance.

If the density of the intake layer 32 is outside the desired values, the article can exhibit excessive leakage and can provide an undesired moist, wet feeling against the wearer's skin. An overly high density can limit the saturation capacity of the intake layer and can provide excessively low permeability. This can excessively slow the acquisition and intake of liquid. Additionally, an overly high density can decrease and inhibit the desired liquid transfer to the absorbent core 30. Insufficient liquid transfer can increase rewet or flowback of liquid to the wearer's skin and can decrease the void volume in the intake layer that is available to absorb a follow-up input of liquid, resulting in an increased likelihood of a premature leak. An overly low density can provide an excessively low web tensile strength and can cause web handling problems. Depending on the basis weight, a low density can provide an excessively thick bulky intake layer that can cause poor comfort and excessive awareness of the product. A low intake layer density can also allow discrete amounts of liquid to be immobilized within the intake structure. This liquid can then be available to increase the likelihood of liquid rewet and flowback to the wearer's skin. Additionally, an overly low density intake structure can provide excessively high permeability. As a result, the properties of liquid control, spreading, distribution and temporary storage can be inadequate. The article can also allow premature leakage or an undesirably moist, wet skin.

Additionally, the intake layer 32 can have a specific, absorbent saturation capacity which is at least a minimum of about 10 grams menses simulant per gram of intake layer material (10 g/g). The specific saturation capacity of the intake layer can alternatively be at least about 10.5 g/g and can optionally be at least about 11 g/g to provide improved performance. In other aspects, the specific saturation capacity of the intake layer can be up to a maximum of about 15 g/g, or more. The specific saturation capacity of the intake layer can alternatively be up to about 14.5 g/g and can optionally be up to about 14 g/g to provide improved effectiveness. In a desired arrangement, the specific saturation capacity of the intake layer can be about 13 g/g.

In a further feature, the intake layer 32 can have a total, absorbent saturation capacity which is at least a minimum of about 0.5 grams of menses simulant (0.5 g). The total saturation capacity of the intake layer can alternatively be at least about 5 g and can optionally be at least about 10 g to provide improved performance. In other aspects, the total saturation capacity of the intake layer can be up to a maximum of about 23 g, or more. The total saturation capacity of the intake layer can alternatively be up to about 22 g and can optionally be up to about 21 g to provide improved effectiveness. In a desired arrangement, the total absorbent saturation capacity of the intake layer can be about 17 grams of menses simulant.

The intake layer 32 of the present invention can be equal to or smaller in size, as compared to the size of the absorbent core 30. For example, the intake layer 32 might have a surface area that is approximately 25-50% of the surface area of the absorbent core 30. The intake layer can desirably be substantially centered (in the longitudinal direction 22 and the transverse direction 24 with respect to the shaping layer, but it may optionally be skewed or offset in a selected direction (e.g., along the longitudinal direction 22), depending on where the liquid is expected to first enter the absorbent article.

The intake layer 32 may have any operative shape and/or design. For example, the intake layer may include a single piece of material, or multiple pieces of material, such as multiple strips of material. In addition, the intake layer 32 may include holes or apertures to better provide desired liquid-intake properties. The apertures may extend partially or completely through the z-directional thickness of the intake layer 32, as desired.

In some aspects, the article 20 can include at least one side cover 77. Side covers are an additional strip of cover material that is positioned longitudinally along a longitudinal side edge of the article. Side covers 77 are often hydrophobic, but they need not be. Suitable materials for side covers include a fibrous material formed from fusible polymeric fibers or filaments. The side cover 77 can be nonperforated, although a perforated web can be used if desired. The side cover 77 can be formed from various polymers, including polyamides, polyesters, polyolefins, polyvinyl acetate, polyvinyl chloride, polyvinyl alcohol, cellulose acetate, viscose, and the like. Suitable materials include polypropylene spunbond and bonded carded webs. In some aspects, the side cover 77 has a uniform web with a denier of about 1.5 or greater. Side covers are also discussed in U.S. Pat. No. 5,415,640 to Kirby et al., which is incorporated herein by reference in a manner that is consistent herewith.

In some aspects of the invention, the article 20 can include a system of side panel or wing portions 42. The side panels can be unitarily formed from a selected component of the article, such as the cover and/or the backsheet, and are integrally connected to appointed sections of the side regions along the intermediate portion 76 of the article. Alternatively, the side panels or wings can be separately provided members that are subsequently attached or otherwise operatively joined to the intermediate portion of the article 20.

The side panels can have an appointed storage position (not shown) in which the side panels 42 are directed generally inwardly toward the longitudinally-extending centerline 52. In some aspects, the side panel that is connected to one side margin may have sufficient cross-directional length to extend and continue past the centerline 52 to approach the laterally opposite side margin of the article. The storage position of the side panels can ordinarily represent an arrangement observed when the article is first removed from its wrapper or other packaging. Prior to placing the article into a bodyside of an undergarment prior to use, the side panels 42 can be selectively arranged to extend laterally from the side regions of the article intermediate portion 76. After placing the article in the undergarment, the side panels 42 can be operatively wrapped and secured around the side edges of the undergarment to help hold the article in place, in a manner well known in the art.

The side panel portions 42 can have any operative construction and can include a layer of any operative material. Additionally, each side panel can comprise a composite material. For example, the side panels may include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web, or the like, as well as combinations thereof.

Each side panel 42 can be joined to its corresponding side region of the article in any operative manner. For example, the side panel can be joined to the cover 26, the backsheet 28 or another article component, as well as any combination thereof. As seen in FIGS. 1-1B, for example, each side panel 42 is joined to the outward, garment-side surface of the backsheet 28, but may optionally be joined to the bodyside surface of the backsheet. The side panel can be attached with hot melt adhesive, but any other operative adhesive or attachment mechanism may alternatively be employed.

In another feature, each side panel portion 42, or any desired combination of the employed side panel portions, can include a panel-fastener component which is operatively joined to an appointed engagement surface of its associated side panel. The panel-fastener component can include a system of interengaging mechanical fasteners, a system of adhesive fasteners, or the like, as well as combinations thereof.

As representatively shown in FIGS. 1-1B, for example, each side panel 42 can include a cooperating component of an interengaging mechanical fastener system. As illustrated, the component can be a "male" component 46 (e.g., a hook component) of the fastener system. Any operative hook component may be employed. For example, a suitable hook component material can include a J-hook, mushroom-head hook, flat-top nail-head hook, a palm-tree hook, a multiple-J hook, or the like, as well as combinations thereof. Alternatively, either or both side panels 42 can include a panel-fastener system which incorporates an operative adhesive. The adhesive may be a solvent-base adhesive, a hot melt adhesive, a pressure-sensitive adhesive, or the like, as well as combinations thereof.

An operative first section of the selected hook component 46 can be joined to a major facing surface of at least a first side panel portion 42 and can be configured to contact or otherwise engage a second side panel portion during ordinary use. Additionally, an operative second section of a hook component, composed of the same or different type of hook material, can be joined to a major facing surface of the second side panel portion and can be configured to contact or otherwise engage an outward surface of the wearer's undergarment during ordinary use. For example, the hook component can be arranged to operatively engage and removably attach to the outward surface of a crotch region of the undergarment.

Each side panel portion 42, or any desired combination of the employed side panel portions, can include a loop or other "female" component 48 of an interengaging mechanical fastener system. Any operative loop component may be employed. For example, a suitable loop component material can include a woven fabric, a knit fabric, a nonwoven fabric, a fabric laminated to a substrate, or the like, as well as combinations thereof.

An operative first section of a selected loop component 48 can be joined to a major facing surface of at least the second side panel portion and can be configured to contact or otherwise engage the hook component 46 on the first side panel portion 42 during ordinary use. Additionally, an operative second section of a loop component, composed of the same or different type of loop material, can be joined to a major facing surface of the first side panel portion 42. As a result, the user can have the option of alternatively attaching the second hook component of the second side panel onto the second loop component of the first side panel. Accordingly, the hook component 46 may alternatively be engaged with the outward surface of the wearer's undergarment.

Each or any desired combination of the provided loop components 48 may be a separately provided member that is subsequently joined and assembled to its corresponding side panel portion 42. In a desired feature, each or any desired combination of the provided loop components can be integrally provided by the material employed to construct its corresponding side panel portion.

In the various arrangements of the present invention, the hook component 46 can be configured to have a particularly selected hook concentration or density (hooks per unit area). In a particular aspect, the hook density can be at least a minimum of about 1500 hooks/in$^2$ (about 232 hooks/cm$^2$). The hook density can alternatively be at least about 2000 hooks/in$^2$ (about 310 hooks/cm$^2$) and can optionally be at least about 3000 hooks/in$^2$ (about 465 hooks/cm$^2$) to provide improved performance. In another aspect, the hook density can be not more than a maximum of about 7000 hooks/in$^2$ (about 1085 hooks/cm$^2$). The hook density can alternatively be not more than about 6000 hooks/in$^2$ (about 930 hooks/cm$^2$) and can optionally be not more than about 5000 hooks/in$^2$ (about 775 hooks/cm$^2$) to provide improved performance.

Examples of suitable hook materials can include 85-Series and 61-Series hook materials available from Velcro, U.S.A., a business having offices located in Manchester, N.H., U.S.A. The hook materials can have a hook density of about 775 hooks/cm$^2$.

In a particular aspect, the material of the loop component 48 may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515 entitled Pattern-Unbonded Nonwoven Web and Process for Making the Same, by T. J. Stokes et al., and granted Jan. 12, 1999; the entire disclosure of which is hereby incorporated by reference in a manner that is consistent herewith.

The complementary components of the mechanical fastener are configured to provide a selected attachment peel-force value. In a particular aspect, the peel-force value can be at least a minimum of about 75 grams (g). The peel-force value can alternatively be at least about 100 g and can optionally be at least about 150 g to provide improved performance. In other aspects, the peel-force value can be up to a maximum of about 300 g, or more. The peel-force value can alternatively be up to about 250 g and can optionally be up to about 225 g to provide improved effectiveness.

The complementary components of the mechanical fastener are also configured to provide a selected attachment shear-force value. In a particular aspect, the shear-force value can be at least a minimum of about 1000 g. The shear-force value can alternatively be at least about 1250 g and can optionally be at least about 1500 g to provide improved performance. In other aspects, the shear-force value can be up to a maximum of about 3500 g, or more. The shear-force value can alternatively be up to about 3000 g and can optionally be up to about 2000 g to provide improved effectiveness.

If the peel-force and/or the shear-force are outside the desired values, the fasteners may experience premature unfastening, or may be too difficult to unfasten to remove the article 20 from an associated undergarment.

In the construction of the article 20, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

Figure 9:
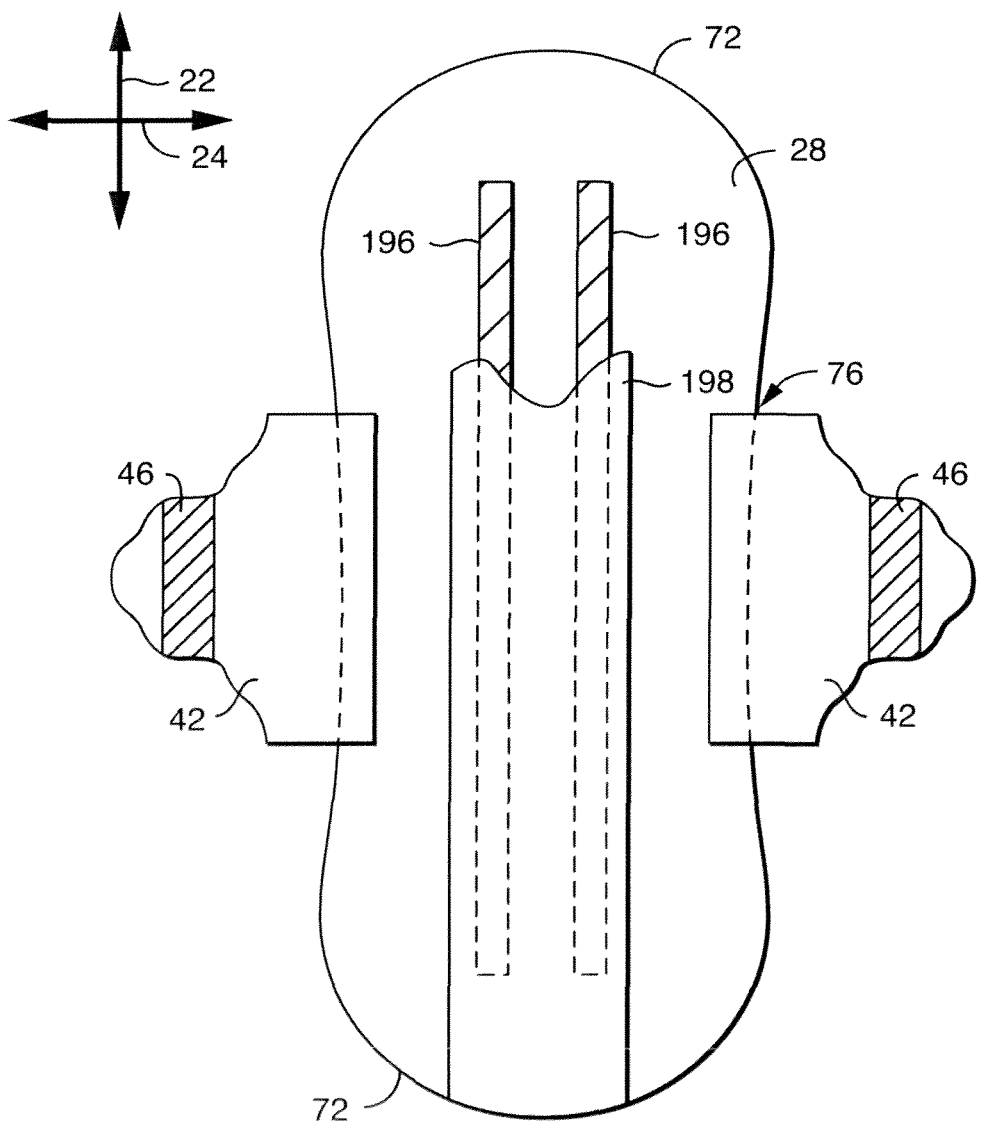
FIG. 9 shows a garment attachment mechanism.

Additionally, as seen in FIG. 9, a selected configuration (e.g., one or more strip regions) of a garment attachment mechanism (e.g., a garment-attachment adhesive 196) may be distributed onto the garment-side of the article to help secure the article to a wearer's undergarment. Typically, the garment adhesive is distributed over the garment-side of the backsheet 28, and one or more layers or sheets of release material 198 are removably placed over the garment adhesive to cover the adhesive for storage prior to use. Optionally, the garment-attachment mechanism can include an operative component of a mechanical fastening system. For example, the garment-attachment mechanism can include an operative component of a "hook-and-loop" type of fastening system.

The article of the present invention includes at least one barrier structure. The barrier structure serves to establish a barrier to leakage from the article, such as side leakage for example, and can help keep the body-facing surface of the feminine care pad and the underlying absorbent material in close proximity to the wearer's body. The barrier structure can be provided in a number of forms, including as a separate structure or as an integrated structure. By integrated structure, it is meant that the barrier structure is located within the pad, rather than being attached as an isolated component to the body-facing surface of the absorbent article.

Figure 1A:
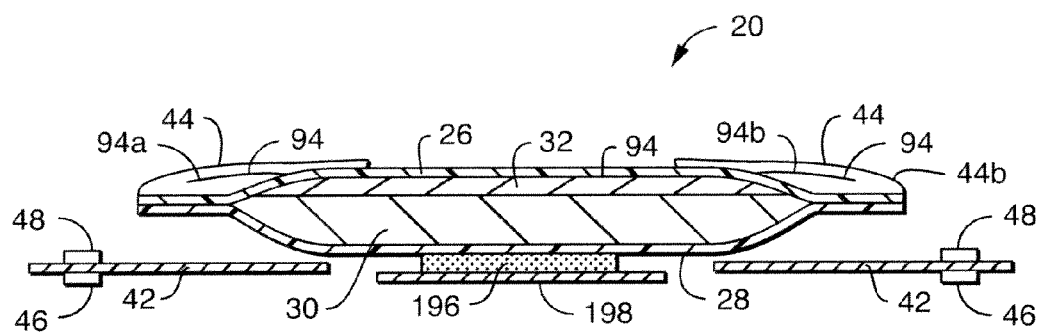
FIG. 1A is a cross-section view of FIG. 1 prior to liquid insult taken along line 53-53.
Figure 1B:
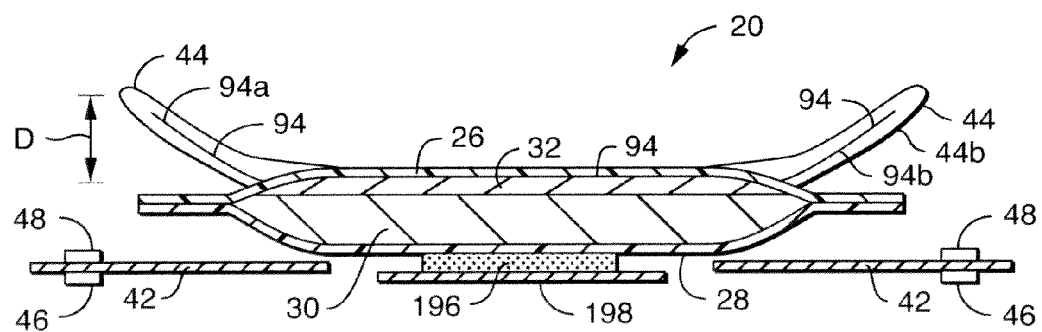
FIG. 1B is the same cross-section view of FIG. 1A after liquid insult taken along line 53-53.

In one aspect of the invention, the feminine care pad 20 shown in FIGS. 1 and 1A is provided with a flat barrier structure 44. If the barrier structure has a radius of curvature, then the radius of curvature toward the wearer's body, the radius of curvature can by as desired, such as up to about 5 mm, for example. However, in some desirable aspects, the barrier structure is relatively flat so as not to draw the attention of the wearer when preparing for use. If the barrier structure 44 is flat, then the radius of curvature is effectively zero.

Figure 2:
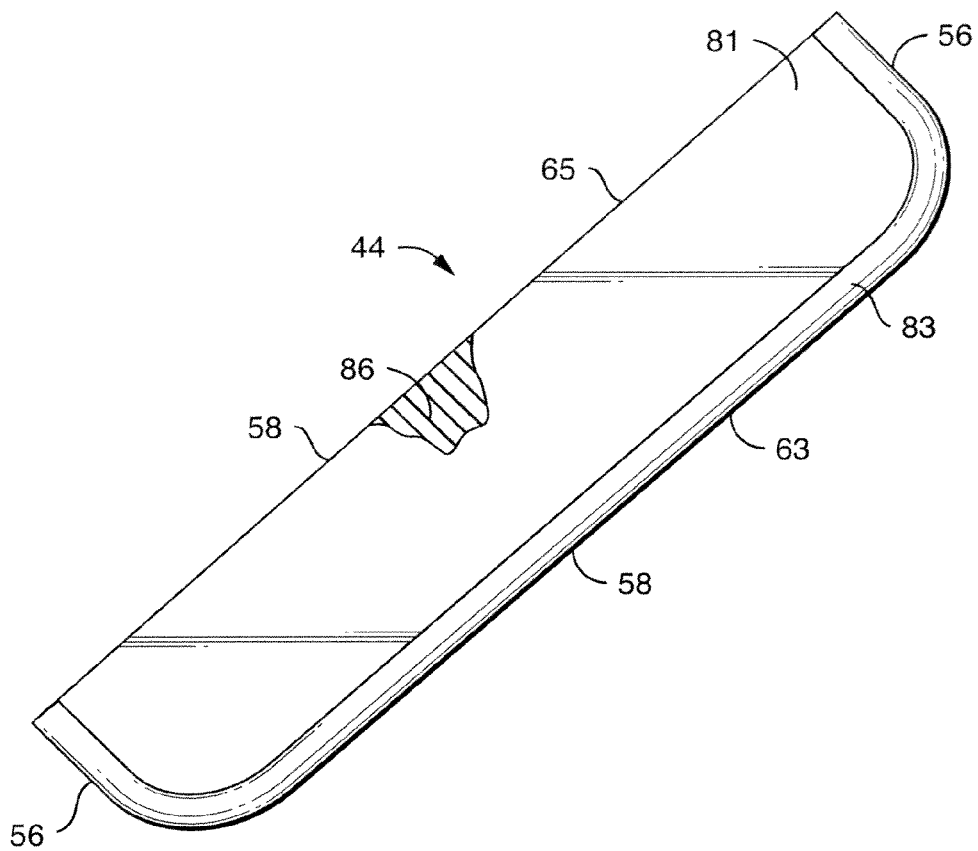
FIG. 2 is a top view of a barrier structure.

The barrier structure can have any shape that is desired. For example, in one aspect, the barrier structure 44 has a rectangular shape, such as seen in FIGS. 1 and 2. In some aspects, one or more of the corners can optionally be rounded. The barrier 44 in this aspect is defined by a pair of longitudinal edges 58 and a pair of ends 56. One longitudinal edge 58 is an inward-facing side 63 and one longitudinal edge 58 is an outward-facing side 65. As used herein with respect to the barrier structure 44, the term "inward facing side" means the longitudinal edge 58 which faces toward the centerline 52 or 53 of the article in the x-y plane, and the term "outward-facing side" means the longitudinal edge 58 which faces away from the centerline 52 or 53 of the article in the x-y plane.

In FIG. 1, a barrier structure 44 is located at each side edge 34 of the article, and each is directed generally inwardly toward the longitudinally-extending centerline 52 of the article. In desirable aspects, the barrier structure 44 is relatively flat, whereas in other aspects the barrier structure 44 can be concave toward the wearer's body in use. In FIG. 1, the barrier structure 44 forms as obstruction to the flow of bodily exudates in the transverse direction. Such exudate movement can lead to staining of the wearer's undergarment and is often referred to as "side leakage." In the embodiment of FIG. 1, the barrier structures 44 are symmetrical about the transverse-extending centerline 53, but they need not be.

FIG. 1 shows one aspect in which the ends 56 of the barrier structures 44 extend longitudinally beyond the side panels of the article. It should be understood that this is merely one aspect of the invention, and that other configurations are also suitable. In general, the longitudinal length of the barrier structure 44 can be any length that is desired for suitable performance of the article.

In some aspects, the barrier structure 44 is located on top of the first major surface 21, such as above the cover 26, if present. In other aspects, the barrier structure 44 is located below the first major surface, such as when the barrier structure 44 is integrated into the article 20. For example, in aspects where a cover is present, the barrier structure 44 can be located between the cover 26 and the backsheet 28, or between the cover 26 and the absorbent core 30 (FIG. 3), or between the cover 26 and optional transfer layer 32. Other configurations for the barrier structure 44 in the article 20 may also be desirable and would be readily apparent to those skilled in the art.

The barrier structure 44 may be liquid pervious, semi-pervious, or liquid impervious, and may be absorbent or nonabsorbent, as desired. Thus, in one aspect of the present invention, when the barrier structure 44 is absorbent, it can provide additional absorbent capacity in the article 20. In still other embodiments, at least one barrier structure 44 can be disposed at various other locations on the article 20, such as oriented in the transverse-extending direction located a distance from one side or another side of the transverse-extending centerline 53 of the article 20, or in a diagonal direction, or any other suitable orientation as desired.

The barrier structure 44 may be of any caliper. However, in some desirable aspects, the caliper of the barrier structure 44 is less than or equal to about 1.5 mm, more preferably less than about 1 mm or less, so that the total caliper of the feminine care pad 20 is less than about 4 mm, such as less than about 3 mm. It is understood, however, that a thicker barrier structure and thicker feminine care pad can also be provided within the scope of the invention.

The barrier structure can be any length as desired and may be dependent on the size of the article. Although the barrier structure 44 is shown as having a length that is only a portion of the length of the feminine care pad 20, in other aspects, the barrier structure 44 can be made up to the full length of the feminine care pad 20, or longer. For example, the barrier structure 44 can range in length from about 25 mm to about 270 mm, such as from about 50 mm to about 200 mm to provide improved performance. In one particular aspect, the length of the barrier structure 44 is about 110 mm. In some desirable aspects, the barrier structure 44 does not extend beyond the dimensions of the pad 20.

The barrier structure also has a width dimension. The barrier structure can be any width desired, and may be dependent on the size of the article. For example, the barrier structure 44 can range in width from about 5 mm to about 40 mm, such as from about 10 to about 30 mm to provide improved performance. In one particular aspect, the width of the barrier structure 44 is about 20 mm.

In general, the barrier structure should be flexible enough so that the absorbent article is comfortable to wear. However, the barrier structure should also be stiff enough to maintain leakage barrier properties when activated. For example, in some aspects, the barrier structure should be laterally compressible under relatively low forces so that the absorbent article is comfortable in use. When worn, feminine care pads and other related catamenial products are subjected to lateral compression forces. The barrier structure 44 should be resilient enough so that the feminine care pad should preferably return to its uncompressed state when these compressive forces are released. This ensures that the barrier structure will remain in close body contact once it has been activated.

The barrier structure 44 comprises a barrier structure member 86. The barrier structure member 86 can be formed from many of the types of materials. For example, the barrier structure member 86 can be formed from soft flexible material such as foam, fluff, gel, silicone, rubber, paper, nonwoven, film, or the like. For instance, absorbent material such as webs or laminates of absorbent material, with or without superabsorbent materials, can be suitable. Examples of suitable absorbent materials also include webs of cross-linked cellulosic fibers and meltblown webs. Alternatively, the insert can be made from impervious materials. Examples of some suitable nonabsorbent materials include thermoplastic polyethylene, polypropylene, synthetic foams, films or suitable blends of the types of materials described herein. In one particular aspect, a thermoplastic foam such as modified polyvinyl alcohol, polyethylene oxide, polypropylene oxide, ethylene oxide-propylene oxide copolymer, polyethylene glycol, polypropylene glycol, ethylene glycol-propylene glycol copolymer, modified polysaccharides, such as hydroxypropyl cellulose, methyl cellulose, methyl ethyl cellulose, polyethylene imine or combinations thereof can be used to make the barrier structure. Suitable foams are described in U.S. patent application Ser. No. 11/117,864 to Zhang et al. and Ser. No. 11/027,306 to Radwanski et al., each of which is hereby incorporated by reference in a manner that is consistent herewith. Other suitable foams are available commercially. For example, foams which retain bulk thickness after hydraulic needling (i.e., resilient foams) include RYNEL 562-B medical grade polyurethane and RYNEL 562-D medical grade polyurethane, both available from Rynel Ltd., Inc. Other suitable foam layers include MINICELL STD crosslinked polyethylene, available from Voltek, Division of Sekisui America Corporation, a business having offices located in Lawrence, Mass., U.S.A.; latex foams such as those described in U.S. Pat. No. 6,627,670 to Mork et al., which is incorporated by reference in a manner that is consistent herewith; High Internal Phase Emulsion (HIPE) foams such as those described in U.S. Pat. No. 5,260,345 to DesMarais et al., which is incorporated herein by reference in a manner that is consistent herewith; and extruded thermoplastic foams such as those described in U.S. patent application Ser. No. 10/729,881 filed Dec. 5, 2003 by Krueger et al. and U.S. Pat. No. 6,071,580 to Bland et al., both of which are incorporated herein by reference in a manner that is consistent herewith.

In some aspects, the barrier structure further comprises a wrap sheet. More particularly, once the barrier structure member has been cut into the desired shape, it can be enveloped in an optional wrap sheet. As seen for example in FIG. 2, a barrier structure member 86 is placed on a wrap sheet 81, and the wrap sheet 81 is folded over the barrier structure member 86 to at least partially cover the barrier structure member 86. Other well known methods for covering the barrier structure member with a wrap sheet are suitable as well. Suitable wrap sheets include, but are not limited to, thin materials such as woven fabric, a nonwoven fabric, a polymer film, a film-fabric laminate, or the like, as well as combinations thereof. Examples of a nonwoven fabric include spunbond fabric, meltblown fabric, coform fabric, a carded web, a bonded-carded-web, a bicomponent spunbond fabric, or the like, as well as combinations thereof. Other examples of suitable materials for constructing the wrap sheet can include rayon, bonded-carded-webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. The wrap sheet 81 should preferably be comfortable and breathable, particularly in configurations where it will be in direct contact with the skin. In some aspects, the wrap sheet can be the same material as the optional cover or the optional backsheet, though it need not be.

In some aspects, the wrap sheet 81 can be folded over the barrier structure member 86 and then bonded to itself to form an encapsulating configuration around the barrier structure member 86, such as seen in FIG. 2. Thus, the barrier structure can also include a bond area 83. Suitable bonding techniques are known in the art, and can include, but are not limited to, adhesives, ultrasonic bonds, crimping or other suitable means. In some aspects, where the feminine care pad 20 has a barrier structure 44 that is integrated into the pad, a wrap sheet may not be desired since the barrier structure member 86 will not be in substantially direct contact with the skin. However, in other aspects where the barrier structure is integrated into the article, a wrap sheet 81 may be desired for various reasons, such as for stain masking purposes, for example. In still other aspects, it may be desired to have the barrier structure member 86 in direct contact with the skin.

Figure 3:
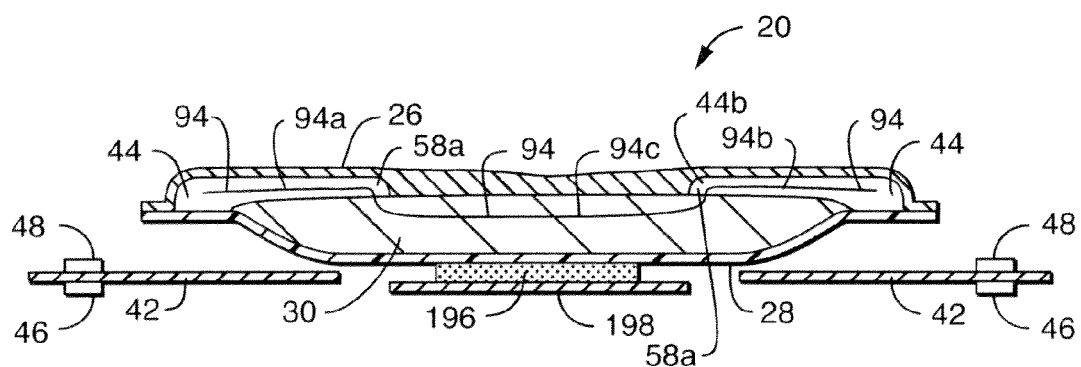
FIG. 3 is a cross-section view of an article of the present invention.

Generally, the barrier structure 44 is attached to the article. In some aspects, the barrier structure 44 is attached to the body-facing side of the cover 26 (if present), such as seen in FIG. 1 and FIG. 1A. In other aspects, the barrier structure 44 can be attached to the garment-facing side of the cover 26 such that the cover 26 is located over the barrier structure 44. In still other aspects, the barrier structure 44 is attached to one of the various other layers or components of the pad 20, such as the absorbent core 30 for example, such as seen in FIG. 3. Attachment of the barrier structure 44 to the article 20 should preferably occur along the longitudinal edge 58a of the barrier structure 44, which is directed generally inwardly toward the longitudinally-extending centerline and/or the transverse-extending centerline of the article 20 (i.e., opposite of the outer edge of the article), depending on the desired configuration of the article, so that the barrier structure 44 can achieve its desired shape when activated. If the barrier structure includes a wrap sheet, it can be desirable to attach the bond area 83 to a component surface of the article 20. Attachment of the barrier structure 44 to a component surface can be accomplished using bonding techniques known in the art including, but not limited to, adhesive bonds, cohesive bonds, thermal bonds, ultrasonic bonds, stitching, or the like, and combinations thereof.

At least one barrier structure 44 can be located in any desired location on the article 20. Preferably, the barrier structure 44 is located on one side or another of the transverse centerline 53, and/or on at least one side of the longitudinal centerline, such as seen in FIG. 1. Preferably, the at least one barrier structure is located outside of the target zone 88 of the absorbent article.

The article of the present invention also includes a liquid-shrinkable string 94. The liquid shrinkable string 94 can be in the form of yarn, fiber, filament, tape, film, nonwoven, laminate, and the like. In desirable aspects, the liquid shrinkable string has a high ratio of length to diameter or width, though it need not be. The liquid shrinkable string 94 is capable of activating the barrier structure 44 to its desired shape upon sufficient fluid contact with the liquid shrinkable string 94. The liquid shrinkable string 94, upon exposure to urine, menstrual fluid or other bodily exudate, will shrink or shorten, thus increasing the tension in the liquid shrinkable string 94. The liquid shrinkable string 94 demonstrates shrinkage ability in both water (urine) and menstrual fluid. Shrinkage of at least about 10%, such as at least about 20%, or at least about 40%, or up to about 60% or more by length is suitable.

Suitable materials for the liquid shrinkable string 94 include modified polyvinyl alcohol (PVA), modified cellulose fibers (e.g., cotton and rayon), such as carboxymethylated cotton, methylated cotton, ethylated cotton, hydroxyethylated cotton, sulfated cotton, sulfonated cotton, phosphated cotton, cationic cotton, amphoteric cotton, sodium acrylate-, acrylic acid-, acrylonitrile- or acrylamide-grafted cellulose fiber and crosslinked fiber thereof; wool or silk modified in the same manner as described above; modified synthetic fiber, such as a partially saponified acrylonitrile series of fiber and vinilon fiber which is partially esterified by maleic acid, carboxymethylcellulose and hydrolyzed acrylic fiber. In one particular aspect, a suitable modified PVA liquid shrinkable string can be obtained from Kuraray Group, Japan (www.kuraray.co.jp/en/).

In some aspects, the liquid shrinkable string 94 can include an optional amount of moisture absorbing polymer. The polymer can be present in the liquid shrinkable string 94 in an amount as desired, provided that it does not diminish the effectiveness of the shrinkable string. For example, in some aspects, the liquid shrinkable string 94 can contain up to about 1 wt %, such as up to about 5 wt %, or even up to about 10 wt % or more moisture absorbing polymer to provide improved benefits. Examples of suitable moisture absorbing polymers include, but are not limited to, polyethylene oxide, polyethylene glycol, polyvinyl alcohol, polyvinyl pyrolidone, polyvinyl pyridine, or mixtures thereof.

In some aspects, the liquid shrinkable string 94 can include an optional elastomeric polymer. The elastomeric polymer may have permeability for water vapor which can facilitate moisture absorption. The elastomeric polymer component should be present in an amount which is effective to achieve the desired dimensional change properties. The elastomeric polymer can be present in an amount as desired, provided that it does not diminish the effectiveness of the shrinkable string. For example, in some aspects, the liquid shrinkable string 94 can contain up to about 1 wt %, such as up to about 5 wt %, or even up to about 10 wt % or more elastomeric polymer to provide improved benefits. Examples of suitable elastomeric polymers include, but are not limited to, thermoplastic polyurethanes, poly(ether-amide) block copolymers, thermoplastic rubbers such as uncrosslinked polyolefins, styrene-butadiene copolymers, silicon rubbers, synthetic rubbers such as nitrile rubber, styrene isoprene copolymers, styrene ethylene butylenes copolymers, butyl rubber, nylon copolymers, spandex fibers comprising segmented polyurethane, ethylene-vinyl acetate copolymer or mixtures thereof. Preferably, the elastomeric polymer is polyurethane.

Figure 7:
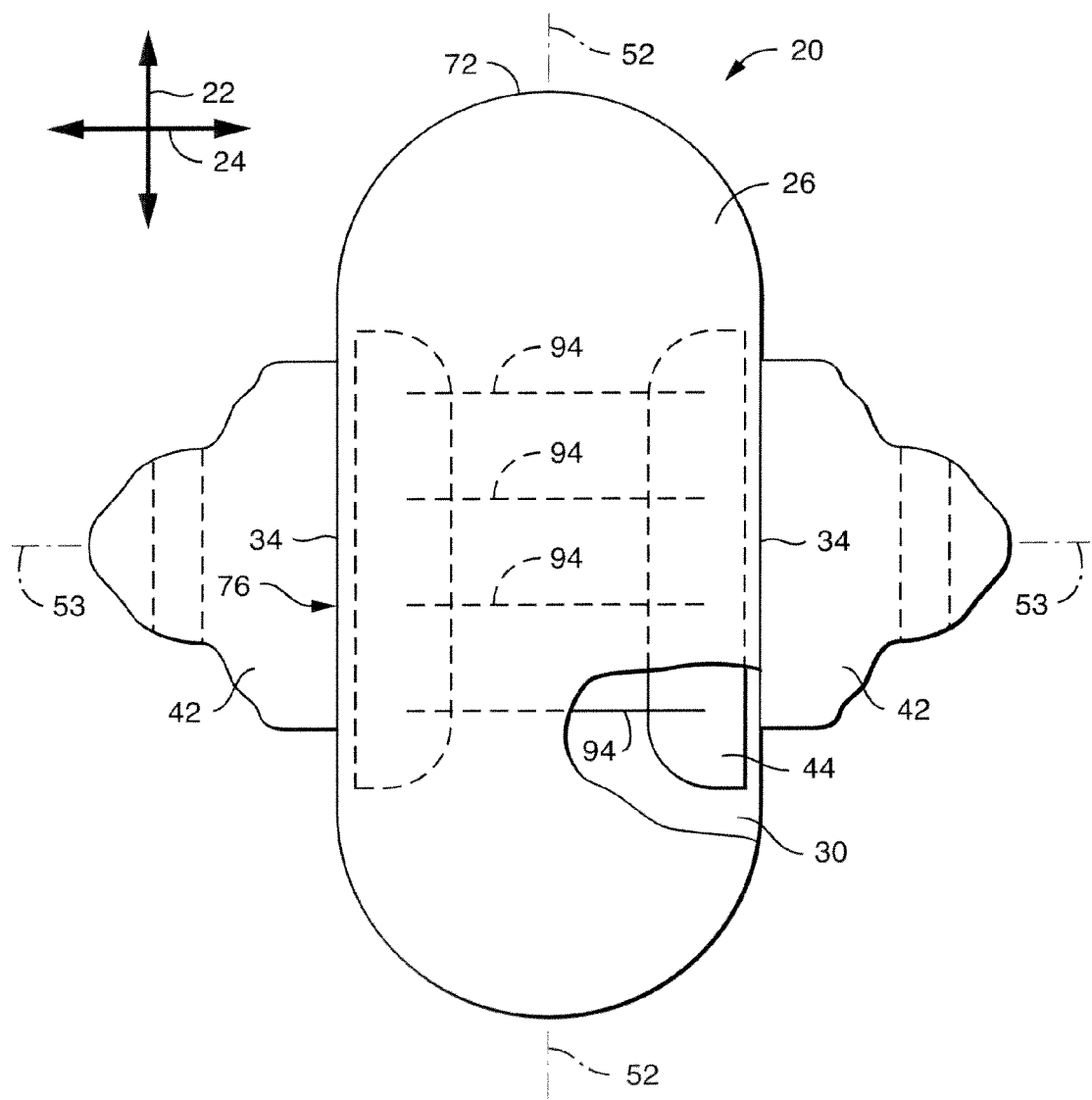
FIG. 7 is a top view of an article of the present invention having a discontinuous stitch pattern.

A first portion 94a of the liquid shrinkable string 94 is desirably attached to the barrier structure 44 (e.g., attached to the surface of the barrier structure, or attached within the structure). In aspects where an additional barrier structure 44b is present, a second portion 94b of the liquid shrinkable string 94 is attached to the additional barrier structure 44b. However, an additional string 97 (i.e., a separate string) can additionally or alternatively be present in the one or more of the barrier structures, such as seen in FIG. 7. Additional, or multiple, strings can each comprise the same material, or they can comprise different materials. FIG. 7 shows a top view of an article of the present invention, having two barrier structures 44 with four separate liquid shrinkable strings 94 attached thereto, such as with adhesive or embossing, for example. In the aspect shown in FIG. 1, the additional barrier structure 44b is shown positioned such that the outward-facing side 65 of the additional barrier structure 44b is positioned adjacent to the second side edge 34a of the absorbent article 20. In other aspects, a portion of the liquid shrinkable string 94 can be attached to another component of the pad 20, such as a cover 26 if present, stabilized absorbent core 30 (such as seen in FIG. 3) or the optional retention layer 32, for example. Attachment of the liquid shrinkable string 94 can occur through bonding techniques known in the art, including, but not limited to, stitching, adhesive bonds, cohesive bonds, thermal bonds, ultrasonic bonds, embossing, crimping, entangling, fusing, or the like, and combinations thereof. In some aspects, such bonding can occur over the entire length of the string. However, in other desirable aspects, at least one desirable portion only of the string can be bonded, such as one or more spot welds with adhesives, for example. In some aspects, it is desirable to anchor the ends of the string into the article or barrier structure, while keeping the central length of the string (e.g., the portion between one or more barrier structures) from bonds to provide improved shrinkage performance.

In one exemplary aspect, the liquid shrinkable string 94 is bonded into the barrier structure 44, such as seen in FIG. 1 and FIG. 3. Any operable stitching pattern can be suitable, provided that it provides the desired shrinkage and lifting of the barrier structure 44. It is understood that the term "stitching pattern" is not limited to stitching or sewing, but also includes bonding techniques known in the art, including, but not limited to, adhesive bonds, cohesive bonds, thermal bonds, ultrasonic bonds, embossing, crimping, entangling, fusing, or the like, and combinations thereof. One suitable stitching pattern can be seen in FIG. 4, which shows a liquid shrinkable string 94 present in barrier structures 44 (represented by phantom lines) where the stitching pattern is in the form of a transverse-extending pattern 80. The stitching may also include an anchor 95 on the ends of the string to help hold the string pattern in place. In some aspects, the spacing between each string in the transverse-extending pattern 80 is approximately equal, though it need not be.

When menstrual fluid or other bodily exudate contacts one or more points of the liquid shrinkable string 94, the total length of the shrinkable string reduces, which creates a tension. The resulting tension pulls up the barrier structure 44 away from the outer edge of the pad 20 inwardly toward the centerline of the pad. In the aspect illustrated in FIG. 1B, two barrier structures 44 are located on either side of the longitudinal-extending centerline 52 adjacent to the edges 34 of the pad 20. In this particular example, using a string pattern similar to that of FIG. 4, a first portion 94a of the liquid shrinkable string 94 is bonded into one of the barrier structures 44, while a second portion 94b of the liquid shrinkable string is bonded into the additional barrier structure 44b, such that the string forms a transverse-extending pattern 80. In some aspects, another portion of the liquid shrinkable string 94c can be bonded into a component of the article, such as in the absorbent core (FIG. 3).

When the strings are contacted by an aqueous fluid, such as urine or menses, the liquid shrinkable string 94 shrinks, which pulls on the barrier structures 44 and lifts them a distance D. The distance D will vary as desired, and will vary with various structure designs. For example, the distance D that a given barrier structure will lift can be at least about 1 mm, such as at least about 4 mm, or at least about 10 mm or more to provide improved benefits. Alternatively, the barrier structure can lift to a desired angle from the plane of the article. For example, the barrier structure can lift to an angle of at least about 10 degrees, such as at least about 30 degrees, or 60 degrees from the plane or more to provide improved benefits. The distance or angle of lift can be modified as desired according to several factors, including the shrinkage ability of the string material, the string position, the stitching pattern, etc. The result is an activated barrier structure which provides a closer body fit, as well as a barrier to leakage.

Figure 5:
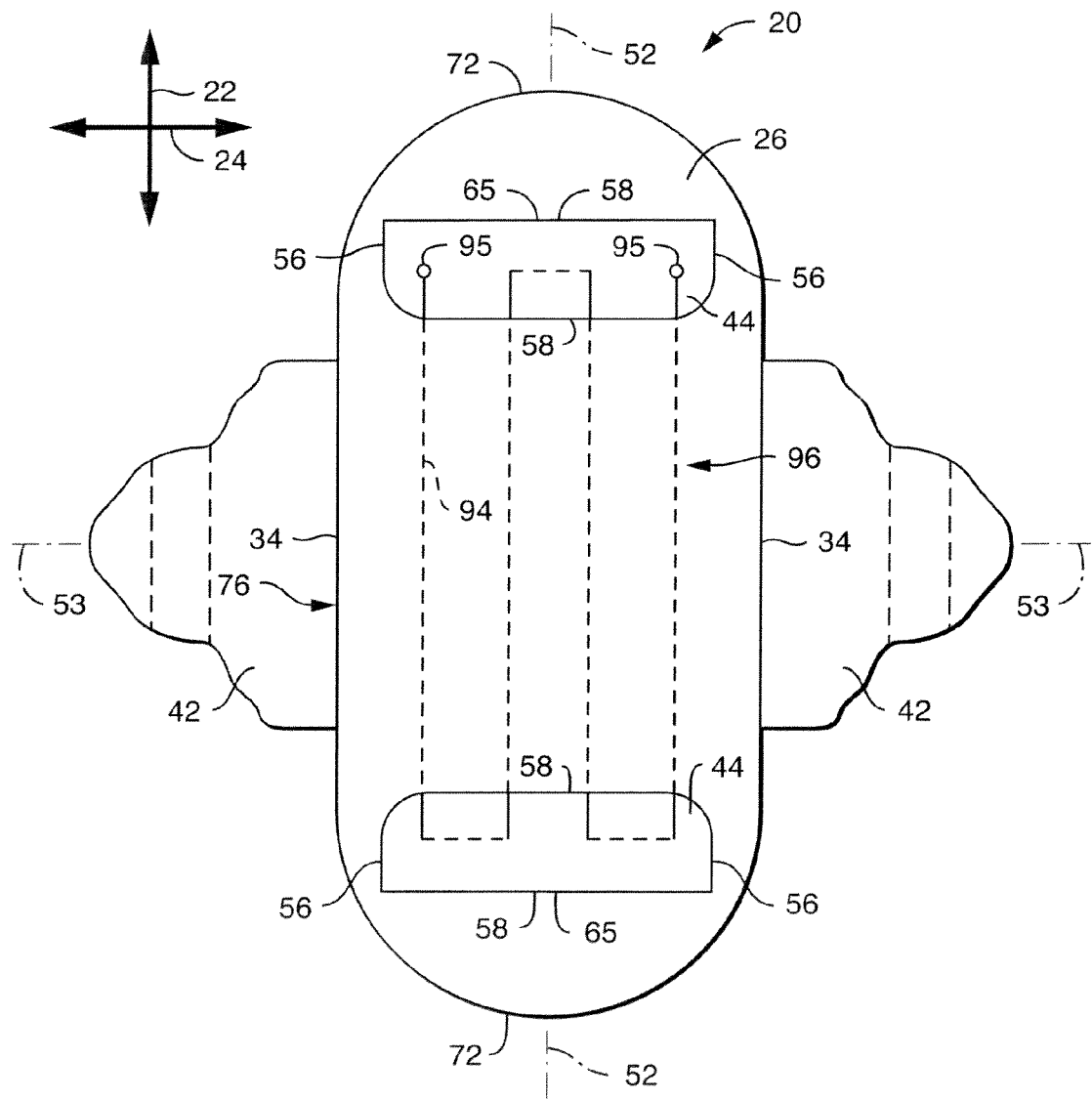
FIG. 5 is a top view of an article of the present invention having a longitudinally-extending shrink material pattern.

In another aspect of the invention, one or more barrier structures 44 can be placed in a transverse orientation on at least one side of the transverse-extending centerline of the pad, such as illustrated in FIG. 5. The liquid shrinkable string 94 is bonded into the barrier structures 44, such as with embossing or adhesive bonds, and optionally into another component of the absorbent article 20, such that the string forms a longitudinally-extending stitching pattern 96. In addition, the ends of the string can be crimped to form anchor points 95 to help hold the bond pattern in place. When the strings are contacted by an aqueous fluid, such as urine or menses, the liquid shrinkable string 94 shrinks, which pulls on the barrier structures 44 and raises them a desired distance to hug the frontal pelvic region and/or rear perineum of the user. The result is an activated barrier structure which provides a closer body fit and a barrier to leakage, such as leakage towards the front and/or the rear.

Figure 6:
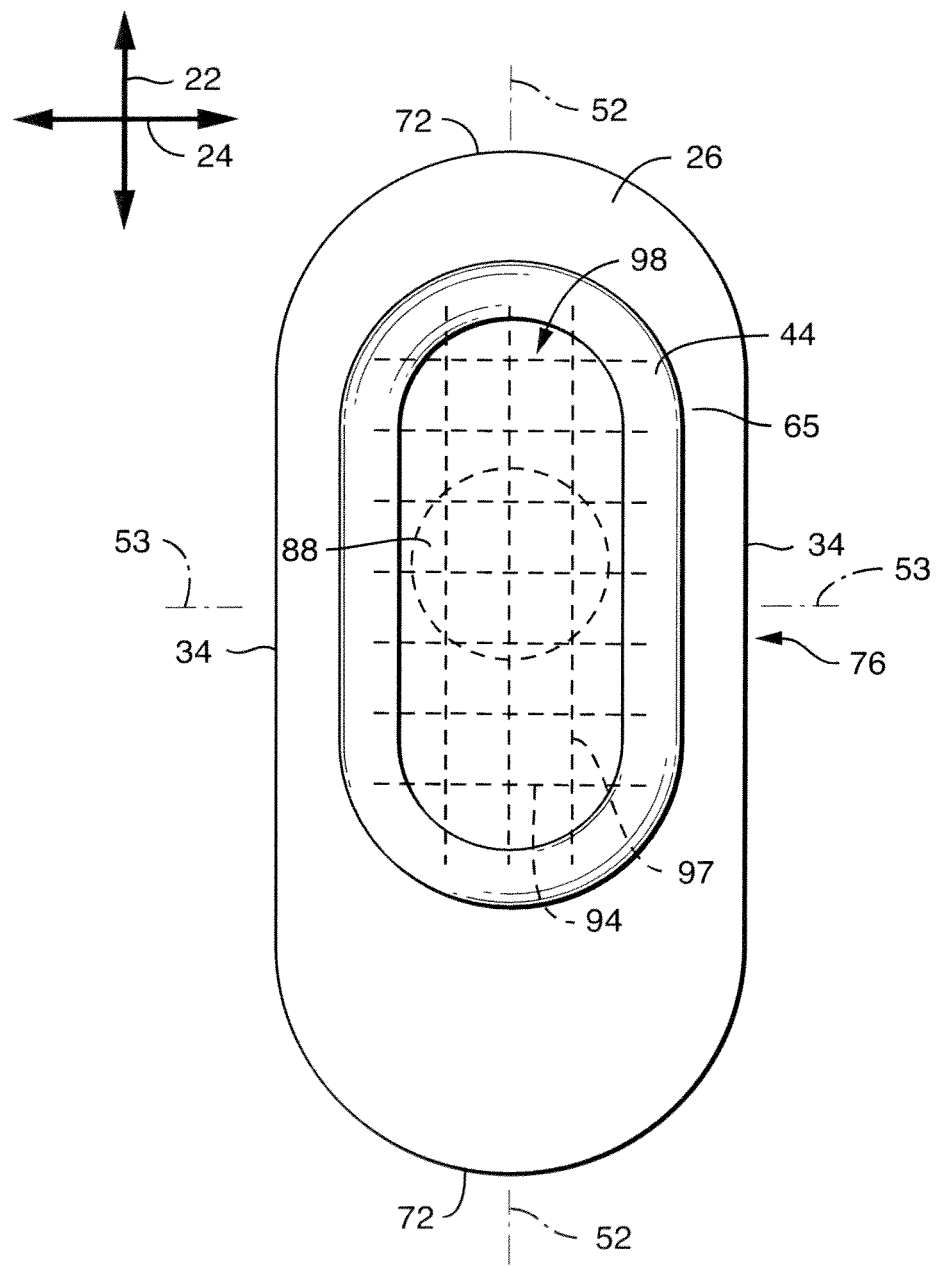
FIG. 6 is a top view of an article of the present invention having a cross shrink material pattern.

In yet another aspect of the invention, one or more barrier structures 44 can be placed around a target zone 88 of the pad, such as illustrated in FIG. 6. For example, a single barrier structure 44 as in FIG. 6 (although there could be more than one) is in the form of a race track-like shape. Liquid shrinkable strings 94 can be bonded in both the transverse-extending direction and the longitudinal-extending direction to form a cross-stitching pattern 98. When the strings are contacted by an aqueous fluid, such as urine or menses, the liquid shrinkable strings 94 shrink, and pull on the barrier structure 44, causing the barrier structure 44 to lift in a 360° fashion, forming a cup-shaped structure that hugs the vulva region of the user. This cup-shaped structure forms a walled fluid containment region that prevents fluid leakage towards the front, rear and sides.

Figure 8:
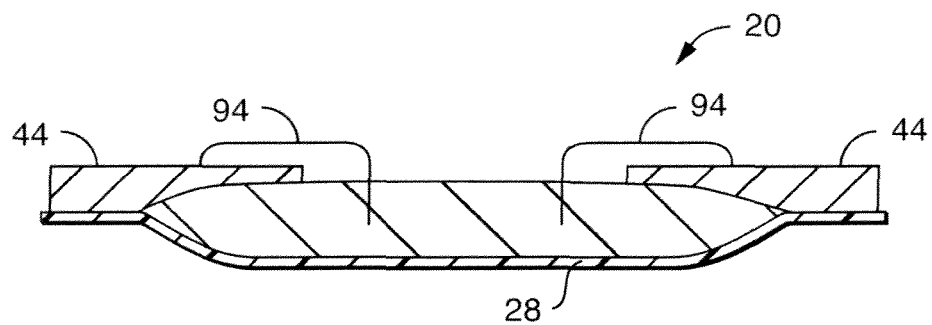
FIG. 8 is a cross-section view of an article of the present invention.

In the preceding various aspects, several exemplary stitch patterns are presented. However, the invention is not limited to these particular stitch patterns, but can include any other various operative patterns understood by those skilled in the art, including, but not limited to, diagonal patterns, wavy patterns, circular patterns, triangular patterns, and the like, for example, without departing from the scope of the invention. In addition, the figures thus far have exemplified strings in a generally planar configuration. However, it is understood that the liquid shrinkable strings 94 can also be present at any angle from plane of the absorbent article, such as seen in, but not limited to, FIG. 8. FIG. 8 shows an absorbent article 20 including two barrier structures 44 attached thereto, wherein two separate liquid shrinkable strings are bonded to the barrier structures and extend therefrom into the absorbent core, substantially perpendicular to the plane of the article 20.

In the preceding various aspects described above, if the barrier structure 44 is located under the cover 26 of the article 20, then it is desirable in some aspects that that cover 26 is operatively affixed to the pad 20 to allow for upward movement of the barrier structure 44 when the liquid shrinkable strings 94 are contacted by liquid. A stretchable cover, as discussed above, can also be suitable for such aspects.

In optional arrangements, the article 20 may include additional components or component layers, as desired. For example, a transfer layer may be positioned between the intake layer 32 and the absorbent core 30. The article can also include other desirable features, such as features that improve the performance of the barrier structures once they have been activated, including but not limited to body adhesives located on the body-facing side of the barrier structures, for example. The article can also have various other configurations, including a de-coupled configuration and those described in U.S. patent application Ser. No. 12/215,535 to McDaniel, which is incorporated herein by reference in a manner that is consistent herewith. Still other article configurations can include folded structures, such as "V" and "W" structures, including those disclosed in U.S. Pat. No. 6,521,811 to Lassen et al., which is incorporated herein by reference in a manner that is consistent herewith.

The present invention may be better understood with reference to the following examples.

EXAMPLES

Example 1

An ultrathin feminine care pad was provided and the cover material was removed. Such a pad can be obtained as currently commercially available KOTEX SOFT & SMOOTH. A flower embossed hydrophobic spunbond side cover material was then cut into two strips each having dimensions of 230 mm×50 mm. The side covers were laid onto the exposed absorbent core (garment-facing side) at opposing side edges of the article such that the side covers aligned longitudinally with the article, with each side cover positioned 15 mm from each longitudinal edge of the pad, thus leaving a portion of the absorbent core exposed in between the side cover strips. The side cover material was a 25 gsm hydrophobic bicomponent spunbond material made from polypropylene/polyethylene (available from Toray Saehan, having a place of business located in Korea). The side covers were each attached to the pad using hot melt adhesive.

Next, a 1.8 mm thick foam material was cut into two strips each having dimensions of 110 mm×15 mm to form barrier structure members. The foam material is available in foam sheets/roll stock under the trade name SEW-1 BLUE, available from Serim TTC, having a place of business in Korea.

An 18 gsm wrap sheet material was then cut into two pieces, each having dimensions of approximately 120 mm×25 mm. The wrap sheet material was a bicomponent nonwoven made from polyethylene/polypropylene, available as SPB4643A from Toray Saehan.

Each foam barrier structure member was then placed onto a wrap sheet such that the barrier structure member and the wrap sheet were longitudinally aligned. Each foam barrier structure member was placed on the wrap sheet such that one longitudinal edge of the barrier structure member was adjacent the longitudinal centerline of the wrap sheet. The wrap sheet was folded over the foam member, resulting in an overhang of approximately 5 mm on one longitudinal side of the foam, and 5 mm on each of the two opposing ends of each foam piece. This overhang was then crimped to enclose each foam piece in each nonwoven wrap, to form two barrier structures.

Each barrier structure was then positioned onto the body-facing side of the pad such that each barrier structure and the pad aligned longitudinally. Each barrier structure was positioned such that the folded (i.e., non-crimped) longitudinal side of the barrier structure was adjacent the longitudinal edge of the pad, with the crimped longitudinal side extending inwardly over the pad toward the longitudinal-extending centerline of the pad. One barrier structure was positioned on each longitudinal edge of the pad, thus leaving a portion of the absorbent core exposed in between the two barrier structures. The barrier structures were substantially centered in the longitudinal direction. Each barrier structure was then attached to the pad using hot melt applied to the bottom of the longitudinal crimped portion of each barrier structure.

Figure 4:
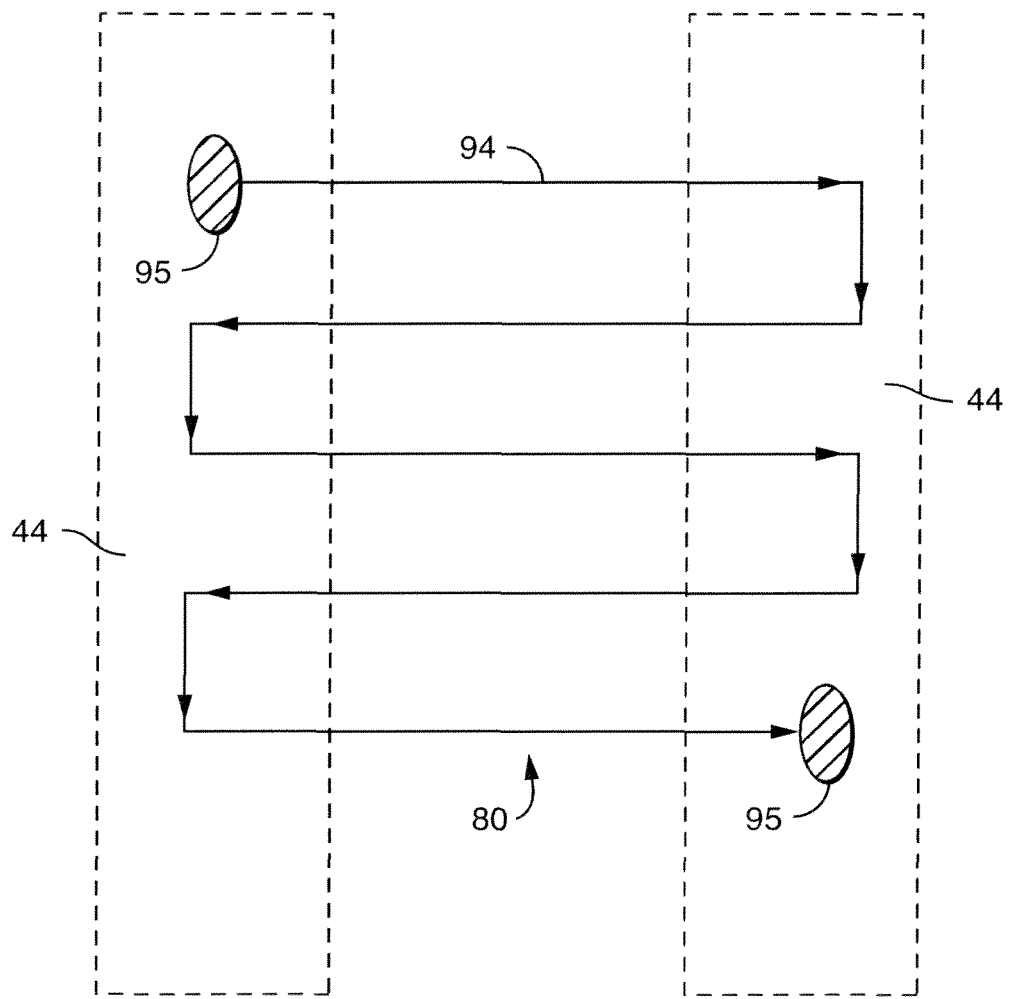
FIG. 4 is an exemplary shrink material pattern.

A single modified polyvinyl alcohol liquid shrinkable string was then stitched (i.e., sewed) through the two barrier structures using a pattern similar to FIG. 4. The string had a length of 400 mm and a diameter of approximately 0.5 mm. The string is available as 2005P10/1T from Kuraray Co., Ltd., having a place of business located in Japan. The single string was stitched between the two barrier structures five times in a transverse-extending pattern, with the distance between each string portion being approximately 25 mm. The stitches extended across the surface of the absorbent core and into each barrier structure a distance of approximately 15 mm from the crimped edge. A knot was formed at the beginning and at the end of the string to provide an anchor for the string and to help hold the stitch pattern in place.

Next, a 24 gsm plain Chisso TABCW nonwoven cover material (available from Da Yuan, China) was cut into an hourglass shape to cover any exposed areas of the pad (i.e., areas not covered by the barrier structures) and then was attached to the pad using hot melt adhesive. The result was a pad that looked generally similar to that of FIG. 1.

Approximately 5 grams of human menses was then applied to the pad in the area of the liquid shrinkable strings. It was noted that the barrier structures each lifted to an angle of approximately 40-50 degrees from the plane of the absorbent article.

Example 2

An ultrathin feminine care pad was provided and the cover material was removed. Such a pad can be obtained as currently commercially available KOTEX SOFT & SMOOTH.

A flower embossed hydrophobic spunbond side cover material was then cut into two strips each having dimensions of 230 mm×50 mm. The side covers were laid onto the exposed absorbent core (garment-facing side) at opposing side edges of the article such that the side covers aligned longitudinally with the article, with each side cover positioned 15 mm from each longitudinal edge of the pad, thus leaving a portion of the absorbent core exposed in between the side cover strips. The side cover material was a 25 gsm hydrophobic bicomponent spunbond material made from polypropylene/polyethylene (available from Toray Saehan, having a place of business located in Korea). The side covers were each attached to the pad using hot melt adhesive.

Next, a 1.8 mm thick foam material was cut into two strips each having dimensions of 110 mm×15 mm to form barrier structure members. The foam material is available in foam sheets/roll stock under the trade name SEW-1 BLUE, available from Serim TTC, having a place of business in Korea.

An 18 gsm wrap sheet material was then cut into two pieces, each having dimensions of approximately 120 mm×25 mm. The wrap sheet material was a bicomponent nonwoven made from polyethylene/polypropylene, available as SPB4643A from Toray Saehan. The wrap sheets were placed a distance apart from the longitudinal edges of each other, where the outside edges of the wrap sheets measured a distance that was approximately equal to the transverse width of the pad.

Four strands of modified polyvinyl alcohol liquid shrinkable string were then bonded with hot melt to the wrap sheets. The strings each had a length of 70 mm and a diameter of approximately 0.5 mm. The string is available as 2005P10/1T from Kuraray Co., Ltd., having a place of business located in Japan. The end portions of each string were bonded onto the surface of the wrap sheets at a location approximately 15 mm from each inner longitudinal edge in an outward direction, with the proximate end of each string being bonded to one wrap sheet, and the distal end of each string being bonded to the other wrap sheet to form a transverse-extending stitch pattern, generally similar to the transverse portions of the stitching pattern shown in FIG. 4. The distance between each string was approximately 25 mm.

The wrap sheet/string assembly was then placed over the two foam barrier structure members, such that each foam barrier structure member was positioned under each wrap sheet, and was oriented in the same longitudinal direction as each wrap sheet, approximately 5 mm from the inner longitudinal edge of each wrap sheet. Each wrap sheet was then folded around its corresponding foam barrier structure member, and the overhanging wrap sheet material (approximately 5 mm on the top and bottom on one longitudinal side edge and on the opposing ends of each barrier structure member) was crimped to envelope each foam barrier structure member.

The barrier structure/string assembly was positioned onto the body-facing side of the pad, such that the folded (i.e., non-crimped) longitudinal side of each barrier structure was adjacent the longitudinal outside edges of the pad, with the crimped longitudinal side of the barrier structures extending inwardly over the pad toward the longitudinal-extending centerline of the pad. The assembly was relatively longitudinally centered on the pad. One barrier structure was positioned on each longitudinal edge of the pad. Each barrier structure was then attached to the absorbent core using hot melt applied to the bottom of the longitudinal crimped portion of each barrier structure. The liquid shrinkable strings stretched across the absorbent core, but were not bonded to the core.

A 24 gsm plain Chisso TABCW nonwoven cover material (available from Da Yuan, China) was then placed over the entire pad and was attached to the pad using hot melt adhesive. The cover was then trimmed to the same dimensions of the pad. The result was a pad that looked generally similar to that of FIG. 7.

Approximately 5 grams of human menses was then applied to the pad in the area of the liquid shrinkable strings. It was noted that the barrier structures each lifted to an angle of approximately 40-50 degrees from the plane of the absorbent article.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. An absorbent article having a longitudinal direction, a transverse direction, a longitudinally-extending centerline, a transverse-extending centerline, first and second longitudinally opposed end portions, and first and second side edges, the absorbent article comprising:
   a. a first major surface which forms a body-facing surface of the absorbent article wherein a cover comprises the first major surface;
   b. a second major surface disposed distally from the first major surface which forms a garment-facing surface of the absorbent article;
   c. an absorbent core positioned between the first major surface and the second major surface;
   d. a barrier structure having an inward-facing side and an outward-facing side wherein the outward-facing side of the barrier structure is positioned adjacent to the first side edge of the absorbent article;
   e. an additional barrier structure having an inward-facing side and an outward-facing side wherein the outward-facing side of the additional barrier structure is positioned adjacent to the second side edge of the absorbent article; and
   f. a liquid shrinkable string;
   wherein the barrier structure and the additional barrier structure are disposed on the first major surface;
   wherein a first portion of the liquid shrinkable string is attached directly to the barrier structure and a second portion of the liquid shrinkable string is attached directly to the additional barrier structure; and
   wherein the inward-facing side of the barrier structure and the inward-facing side of the additional barrier structure are attached directly to the body-facing surface of the cover.

2. The absorbent article of claim 1 wherein the barrier structure comprises a barrier structure member selected from foam, fluff, gel, silicone, rubber, paper, nonwoven or film.

3. The absorbent article of claim 2 wherein the barrier structure further comprises a wrap sheet.

4. The absorbent article of claim 3 wherein the barrier structure comprises a bond area.

5. The absorbent article of claim 4 wherein the bond area is crimped.

6. The absorbent article of claim 1 wherein the liquid shrinkable string is present as a transverse-extending stitching pattern.

7. The absorbent article of claim 6 wherein a spacing within the transverse-extending stitching pattern is approximately equal.

8. The absorbent article of claim 1 wherein the barrier structure is positioned around a target zone of the absorbent article.

9. The absorbent article of claim 8 wherein the liquid shrinkable string is present as a cross stitching pattern.

10. The absorbent article of claim 1 further comprising additional strings that are separately attached to the barrier structure and to the absorbent article.

11. The absorbent article of claim 1 further comprising side panels for attaching the absorbent article to an undergarment.

12. The absorbent article of claim 1 further comprising a garment fastening system for attaching the absorbent article to an undergarment.

13. The absorbent article of claim 1 further comprising at least one of an intake layer, a backsheet and/or a side cover.

14. The absorbent article of claim 1 wherein the absorbent article is a feminine care pad.

15. The absorbent article of claim 1 further comprising multiple liquid shrinkable strings.

16. An absorbent article having a longitudinal direction, a transverse direction, a longitudinally-extending centerline, a transverse-extending centerline, first and second longitudinally opposed end portions, and first and second side edges, the absorbent article comprising:

a. a first major surface which forms a body-facing surface of the absorbent article wherein a cover comprises the first major surface;

b. a second major surface disposed distally from the first major surface which forms a garment-facing surface of the absorbent article;

c. an absorbent core positioned between the first major surface and the second major surface;

d. a barrier structure positioned on one side of the transverse-extending centerline, wherein the barrier structure is in a transverse orientation;

e. an additional barrier structure positioned on the other side of the transverse centerline of the absorbent article, wherein the additional barrier structure is in the transverse orientation; and f. a liquid shrinkable string;

wherein the barrier structure and the additional barrier structure are disposed on the first major surface and the barrier structure and the additional barrier structure are attached directly to the body-facing surface of the cover along a longitudinal edge of each of the barrier structures, each longitudinal edge being directed generally inwardly toward the transverse-extending centerline; and wherein a first portion of the liquid shrinkable string is attached directly to the barrier structure and a second portion of the liquid shrinkable string is attached directly to the additional barrier structure.

17. The absorbent article of claim 16 wherein the liquid shrinkable string is present as a longitudinally-extending stitching pattern.

\* \* \* \* \*